(12) United States Patent
Arias et al.

(10) Patent No.: US 10,548,519 B2
(45) Date of Patent: Feb. 4, 2020

(54) REFLECTANCE BASED PULSE OXIMETRY SYSTEMS AND METHODS

(71) Applicant: The Regents of the University of California, Oakland, CA (US)

(72) Inventors: Ana Claudia Arias, Berkeley, CA (US); Claire Lochner, Berkeley, CA (US); Adrien Pierre, Berkeley, CA (US); Yasser Khan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 240 days.

(21) Appl. No.: 15/414,397

(22) Filed: Jan. 24, 2017

(65) Prior Publication Data

US 2017/0156651 A1 Jun. 8, 2017

Related U.S. Application Data

(63) Continuation of application No. PCT/US2015/042107, filed on Jul. 24, 2015, which is
(Continued)

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0205* (2013.01); *A61B 5/6815* (2013.01); *A61B 5/6826* (2013.01); *A61B 5/024* (2013.01)

(58) Field of Classification Search
CPC . A61B 5/14552; A61B 5/0205; A61B 5/6815; A61B 5/6826; A61B 5/024
See application file for complete search history.

(56) References Cited

U.S. PATENT DOCUMENTS

| 4,167,331 A | 9/1979 | Nielsen |
| 4,807,630 A | 2/1989 | Malinouskas |

(Continued)

OTHER PUBLICATIONS

Sekitani et al., "Flexible Organic Transistors and Circuits with Extreme Bending Stability", NMAT, vol. 9, pp. 1015-1022, 2010.*
(Continued)

*Primary Examiner* — Eric F Winakur
(74) *Attorney, Agent, or Firm* — Leydig, Voit & Mayer, Ltd.; Gerald T. Gray

(57) ABSTRACT

Pulse oximeter devices include a first light emitting element that emits red light, a second light emitting element that emits green light or IR light; and a sensor element that detects red and green (or IR) light and that outputs signals representing detected red and green (or IR) light. The pulse oximeter device further includes a flexible substrate, wherein the first light emitting element, the second light emitting element and the sensor element are formed on the flexible substrate. The sensor element is configured to detect the emitted red and green light transmitted through tissue containing blood, and in certain aspects, the sensor element is configured to detect the emitted red and green (or IR) light reflected by tissue containing blood. A signal processing element (e.g., a processor) receives and processes the signals representing detected red and green (or IR) light output by the sensor element to produce signals representing blood oxygenation content.

17 Claims, 14 Drawing Sheets

Related U.S. Application Data a continuation of application No. 62/028,720, filed on Jul. 24, 2014.

(51) Int. Cl.
*A61B 5/00* (2006.01)
*A61B 5/024* (2006.01)

(56) References Cited

U.S. PATENT DOCUMENTS

| | | | | |
|---|---|---|---|---|
| 5,040,539 | A | 8/1991 | Schmitt et al. | |
| 5,791,345 | A * | 8/1998 | Ishihara | A61B 5/0261 356/39 |
| 5,830,137 | A | 11/1998 | Scharf | |
| 6,330,468 | B1 | 12/2001 | Scharf | |
| 2007/0129613 | A1 | 6/2007 | Rochester et al. | |
| 2011/0112379 | A1 * | 5/2011 | Li | A61B 5/14552 600/300 |
| 2013/0133822 | A1 * | 5/2013 | Koetse | H05K 13/00 156/247 |
| 2013/0261415 | A1 * | 10/2013 | Ashe | A61B 5/14552 600/324 |
| 2016/0302674 | A1 * | 10/2016 | Moyer | A61B 5/02055 |

OTHER PUBLICATIONS

Mendelson, "Pulse Oximetry", Wiley Encyclopedia of Biomedical Engineering, pp. 1-18, 2006.*

International Preliminary Report on Patentability issued in PCT/US2015/042107 dated Jan. 24, 2017.

Yindar Chuo et al. "Platform for All-Polymer-Based Pulse-Oximetry Sensor", IEEE Sensors 2010 Conference, School of Engineering Science, pp. 155-159.

Wj Cui et al., "In Vivo Reflectance of Blood and Tissue as a Function of Light Wavelength", IEEE Trans Biomed Eng., 190, Jun:37(6):632-9.

Rasmus G. Haahr, "An Electronic Patch for Wearable Health Monitoring by Reflectance Pulse Oximetry", IEEE Transactions on Biomedical Circuits and Systems, pp. 1-9.

Sandberg et al. "Non-invasive Monitoring of Muscle Blood Perfusion by Photoplethysmography: Evaluation of a New Application", Acta Physiol Scand, 2005:183, 335-343.

Tamura et al, "Wearable Photoplethysmographic Sensors—Past and Present", Electronics, 2014:3:282-302, ISSN 2079-9292.

International Search Report and Written Opinion dated Oct. 19, 2015, International Application No. PCT/US2015/042107.

* cited by examiner

FIG. 3 Fabrication process for printing organic LEDs and photodiode(s)

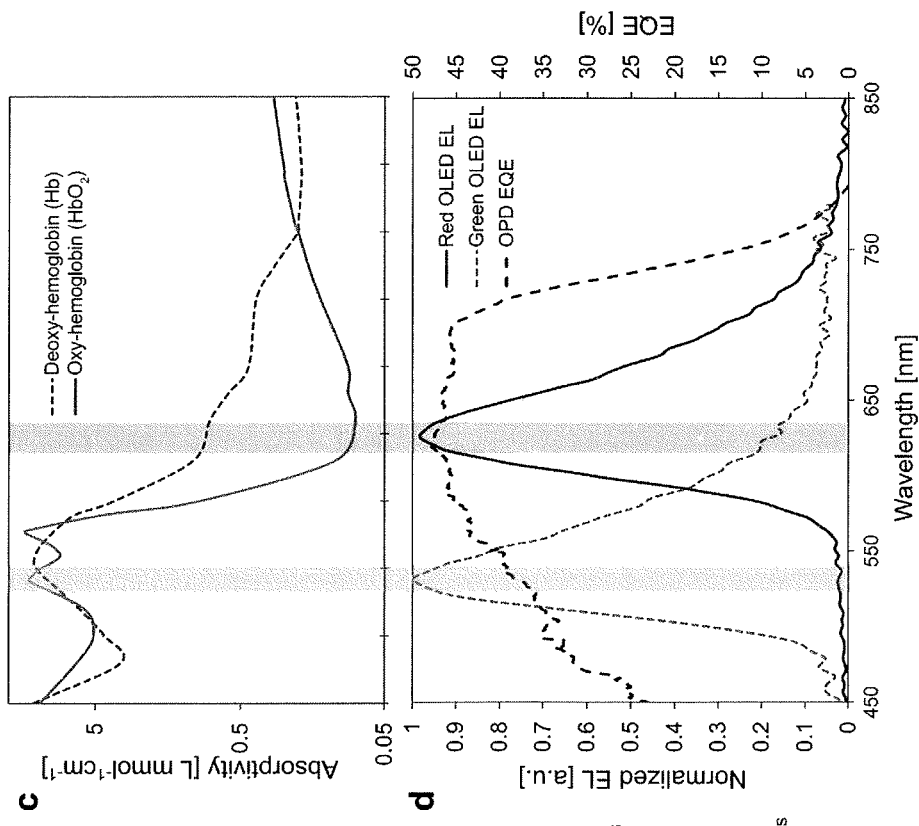
FIG. 7A
FIG. 7B
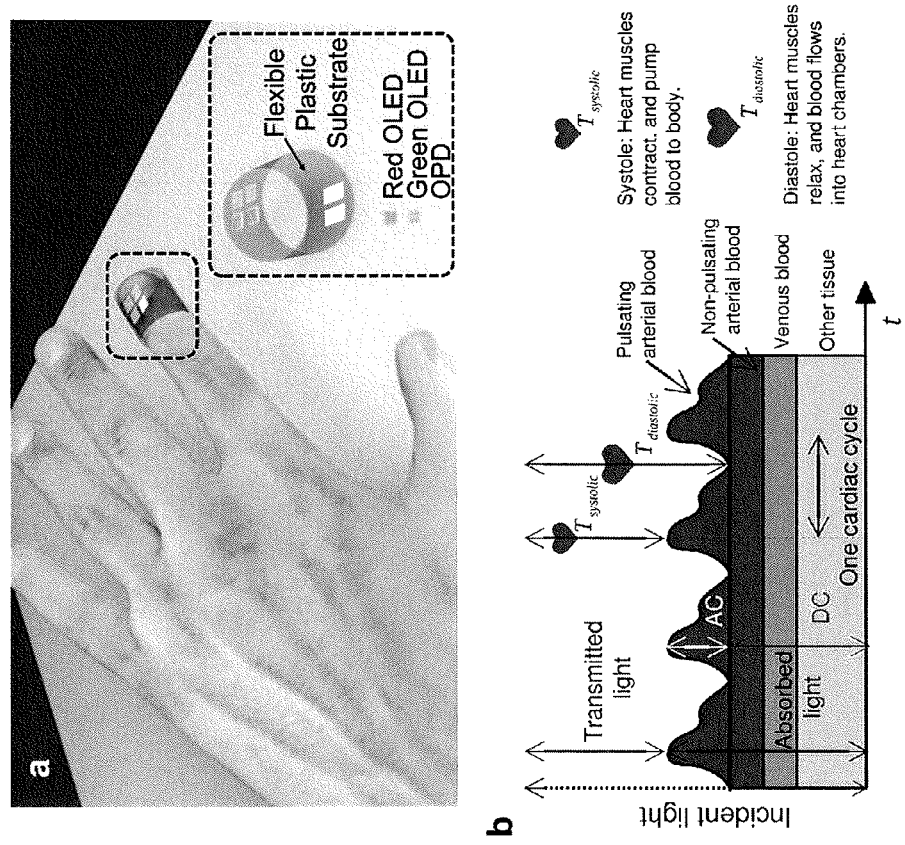
FIG. 7C
FIG. 7D a FIG. 8A
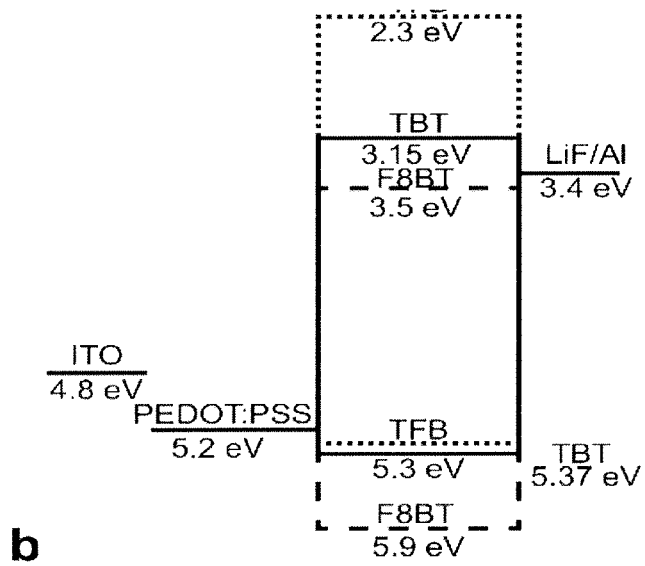
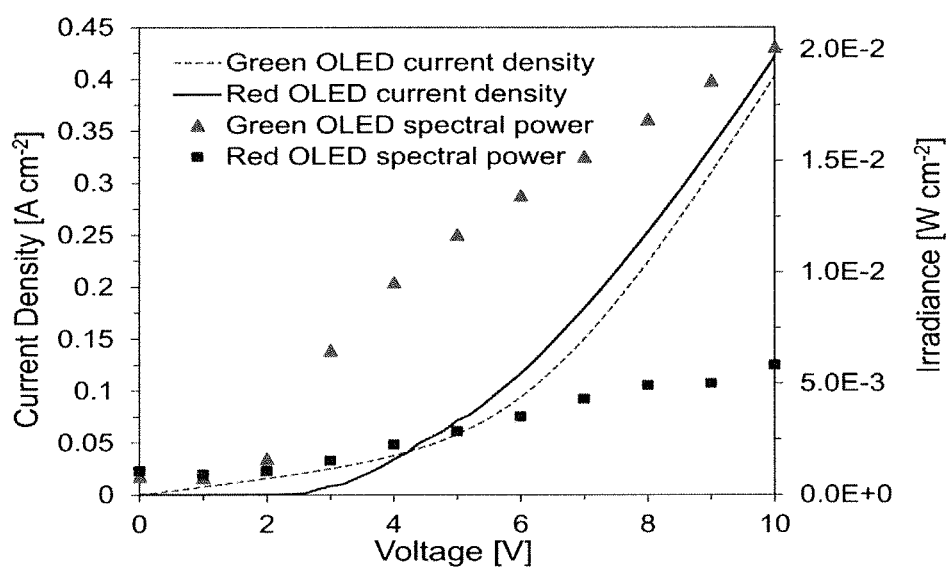
FIG. 8B FIG. 11A
FIG. 11B
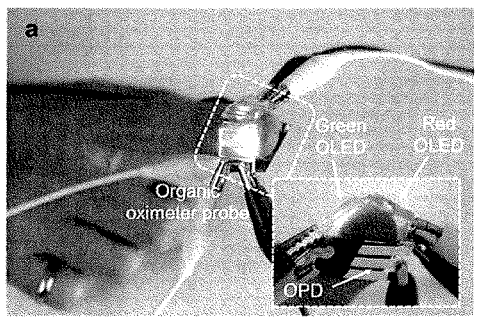
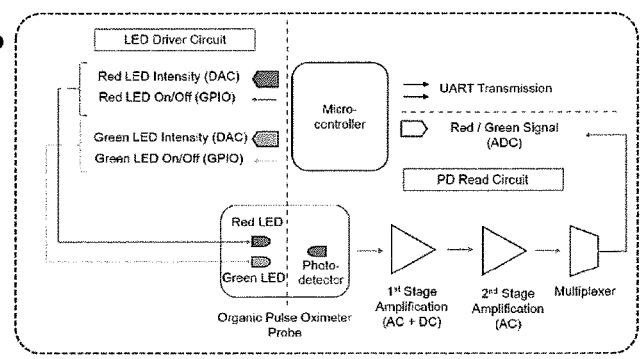
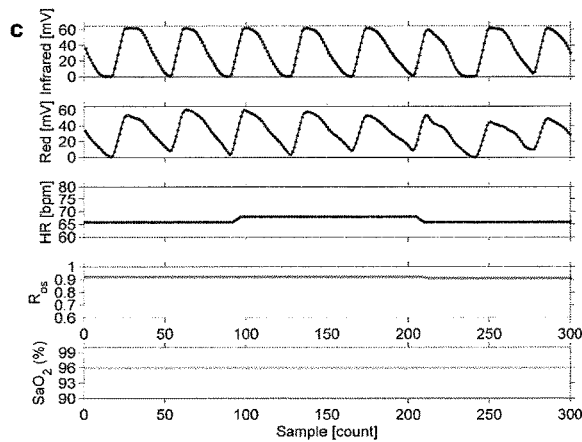
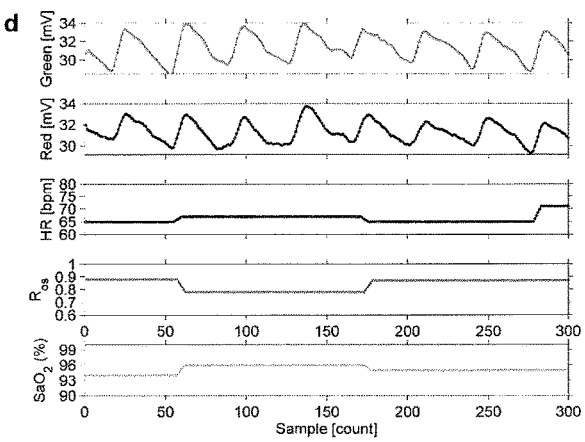
FIG. 11C
FIG. 11D ITO Coated Glass OLED Structure

PEN

OPD Structure

REFLECTANCE BASED PULSE OXIMETRY SYSTEMS AND METHODS

CROSS-REFERENCE TO RELATED APPLICATIONS

This patent application is a continuation of PCT application PCT/US2015/042107, filed Jul. 24, 2015, which claims the benefit of U.S. Provisional Patent Application No. 62/028,720, filed Jul. 24, 2014, which are each incorporated by reference in its entirety for all purposes.

FEDERALLY SPONSORED RESEARCH OR DEVELOPMENT

This invention was made with government support under Grant Number DGE1106400 awarded by the National Science Foundation and Army/ARO Grant Number W911NF-09-3-0001 The government has certain rights in the invention.

BACKGROUND

The present disclosure provides systems and methods to measure pulse and blood oxygen saturation in humans using reflectance spectroscopy.

A blood oximeter measures oxygen saturation percentage in human blood by comparing the amount of light absorbed by the blood (which has different molar extinction coefficients depending on the incident light's wavelength and whether or not the hemoglobin is oxygenated or deoxygenated) at two different wavelengths. Ideally, the molar extinction coefficients of oxygenated and deoxygenated blood will differ substantially at each of the two wavelengths used. Traditionally, red and infrared light is transmitted through human tissue (e.g., ear or finger) and detected to determine oxygen saturation. LEDs are placed on one side of the tissue and a detector placed on the other side. Sampling of the transmitted light provides information about the ratio of oxygenated and deoxygenated hemoglobin in the blood. Such pulse oximeters, however, tend to be bulky and rigid and their use limited to certain tissue areas where sufficient light transmission in the red and IR wavelengths can occur.

SUMMARY

The present disclosure provides systems and methods to measure pulse and blood oxygen saturation in humans using reflectance spectroscopy. In certain embodiments, the systems and methods use solution processed Light Emitting Diodes (LEDs), such as organic light emitting diodes (OLEDs) and solution processed photodetectors, such as organic polymer photodiodes (OPDs). As these organic materials are solution processable they advantageously allows for forming arrays of one or more LEDs and photodetectors onto flexible substrates. For example, in certain embodiments, OLEDs and OPDs are printed on a flexible substrate to form flexible blood oximeters. The flexible blood oximeters of the present disclosure are advantageously able to fit to a variety of form factors, increasing the possible applications of blood oximetry and making the application of monitoring oxygen saturation in a medical patient (e.g., from the patient's ear or finger) less sensitive to motion. Furthermore, the organic LED and photodetector blood oximeter sensors can be produced in an inexpensive manner and can be disposable, ideal for use in medical care environments where sanitation is paramount.

In the present blood oximeter embodiments, two different wavelengths of light (e.g., red and green, or red and infrared) illuminate, or are input onto, an area of human tissue by the OLEDs, and reflected light is recorded by the organic photodetector. The light emitting elements and the sensor or detector element(s) can be positioned on opposite sides of the tissue and traditional transmission measurements made, albeit with red and green light, or the light emitting elements and the detector element(s) can be positioned on the same side of the tissue wherein reflection measurements are made. Red and infrared light may be used in reflectance measurements according to the present embodiments. The output signal of the detector element is processed by pulse oximetry circuitry and software, and the test subject's pulse waveform and blood oxygen saturation percentage is output. Embodiments with the sensors and the light emitting elements positioned on the same side of the tissue to allow for reflection measurements advantageously allow for positioning of a sensor virtually anywhere on a subject's skin.

According to an embodiment, a pulse oximeter device is provided that typically includes a first light emitting element that emits red light, a second light emitting element that emits green light; and a sensor element that detects red and green light and that outputs signals representing detected red and green light. In certain aspects, the first light emitting element includes a first light emitting diode (LED), the second light emitting element includes a second LED, and the sensor element includes a photodetector. In certain aspects, each of the first and second LEDs comprises an organic LED, and the photodetector comprises an organic photodiode. In certain aspects, the pulse oximeter device further includes a flexible substrate, wherein the first light emitting element, the second light emitting element and the sensor element are formed on the flexible substrate. In certain aspects, the sensor element is configured to detect the emitted red and green light transmitted through tissue containing blood, and in certain aspects, the sensor element is configured to detect the emitted red and green light reflected by tissue containing blood. In certain aspects, the pulse oximeter device further includes a signal processing element (e.g., a processor) that receives and processes the signals representing detected red and green light output by the sensor element to produce signals representing blood oxygenation content.

According to another embodiment, a pulse oximeter device is provided that includes a plurality of first light emitting elements that emit red light, a plurality of second light emitting elements that emit green light; and a plurality of sensor elements that detects red and green light and that output signals representing detected red and green light. In certain aspects, the first light emitting elements comprise first light emitting diodes (LEDs), the second light emitting elements comprise second LEDs, and the sensor elements include photodetectors. In certain aspects, each of the first and second LEDs comprises an organic LED, and the photodetectors include organic photodiodes. In certain aspects, the pulse oximeter device further includes a flexible substrate, wherein the first light emitting elements, the second light emitting elements and the sensor elements are formed on the flexible substrate. In certain aspects, the sensor elements are configured to detect the emitted red and green light transmitted through tissue containing blood, and in certain aspects, the sensor elements are configured to detect the emitted red and green light reflected by tissue containing blood. In certain aspects, the pulse oximeter device further includes a signal processing element (e.g., a processor) that receives and processes the signals representing detected red and green light output by the sensor elements to produce signals representing blood oxygenation content.

According to a further embodiment, a method is provided for method of measuring blood oxygenation content of a tissue sample. The method typically includes applying a flexible pulse oximeter device proximal the tissue sample, the pulse oximeter device including a flexible substrate, at least one first light emitting element formed on the substrate that emits red light, at least one second light emitting element formed on the substrate that emits green light or infrared light, and at least one sensor element formed on the substrate that detects red and green light or red and infrared light and that outputs signals representing detected red and green light or detected red and infrared light. The method also typically includes activating the at least one first light emitting element and the at least one second light emitting element, detecting red and green light or red and infrared light reflected by the tissue by the at least one sensor element, and outputting signals representing the detected reflected red and green light or the detected red and infrared light to a signal processing device. In certain aspects, each of the at least one first and second light emitting elements comprises an organic LED, and the at least one sensor comprises an organic photodiode.

According to yet another embodiment, a method is provided for mapping blood oxygenation content of a region of a tissue sample. The method typically includes applying a flexible pulse oximeter device proximal the tissue sample, the pulse oximeter device including a flexible substrate, an array of first light emitting elements formed on the substrate that emit red light, an array of second light emitting elements formed on the substrate that emit green light or infrared light, and an array of sensor elements formed on the substrate that detects red and green light or that detects red and infrared light and that outputs signals representing detected red and green light or detected red and infrared light. The method typically includes activating a first portion of the array of first light emitting elements and a first portion of the array of second light emitting elements, detecting red and green light or red and infrared light reflected by the tissue by a first sensor element, and outputting signals representing the detected reflected red and green light or the detected reflected red and infrared light to a signal processing device. The method also typically includes repeating steps of activating, detecting and outputting for a second portion of the array of first light emitting elements, second light emitting elements and a second sensor element.

BRIEF DESCRIPTION OF THE SEVERAL VIEWS OF THE DRAWING(S)

The accompanying drawings incorporated in and forming a part of the specification illustrate several aspects of the present disclosure and, together with the description, serve to explain the principles of the disclosure. In the drawings:

FIG. 7A shows a pulse oximetry sensor composed of two organic light emitting diode (OLED) arrays and an organic photodiode (OPD) according to an embodiment.

FIG. 7B shows the light transmission path through pulsating arterial blood, non-pulsating arterial blood, venous blood, and other tissues over several cardiac cycles for the oximeter of FIG. 7A. The AC and DC components of the blood and tissue are designated, as well as the peak and trough of transmitted light during diastole and systole, respectively.

FIG. 7C shows absorptivity of oxygenated (orange solid line) and deoxygenated (blue dashed line) hemoglobin in arterial blood as a function of wavelength. The wavelengths corresponding to the peak OLED electroluminesce (EL) spectra are highlighted to show that there is a difference in deoxy- and oxyhemoglobin absorptivity at the wavelengths of interest.

FIG. 7D shows OPD external quantum efficiency (black dashed line) at short circuit, and EL spectra of red (red solid line) and green (green dashed line) OLEDs.

FIG. 8A shows an OLED energy structure.

FIG. 8B shows current density of red (red solid line) and green (green dashed line) OLEDs and spectral power of red (red squares) and green (green triangles) OLEDs as a function of applied voltage.

FIG. 11A shows an organic optoelectronic pulse oximetry system, with red and green OLEDs are placed on subject's finger and transmitted light is collected with one OPD pixel placed below the finger.

FIG. 11B shows a hardware block diagram for the system setup—a microcontroller acts as the data acquisition and processing unit. OLEDs are triggered and controlled using general-purpose input/output port (GPIO) and digital-to-analog converter (DAC) pins, and the OPD signal is recorded using the analog-to-digital converter (ADC) of the microcontroller. A two-stage amplifier between the OPD and ADC removes the DC part from the PPG signal and amplifies the pulsating PPG signal.

FIGS. 11C and 11D shows simultaneous oximetry measurements with a commercially available inorganic oximeter probe and the organic oximeter probe, respectively. The PPG signal was obtained using red and infrared light for the commercially available probe (C), and using red and green light for the organic probe (D). Heart rate (HR) (magenta line in C and D) was obtained by timing the systolic peaks in the PPG signals. The ratio of the transmitted light at two wavelengths ($R_{os}$) (blue line in C and D) is converted to arterial blood oxygen saturation ($S_aO_2$) (yellow line in c and D) using Beer-Lambert's Law in conjunction with an empirical correction.

Figure 12A:
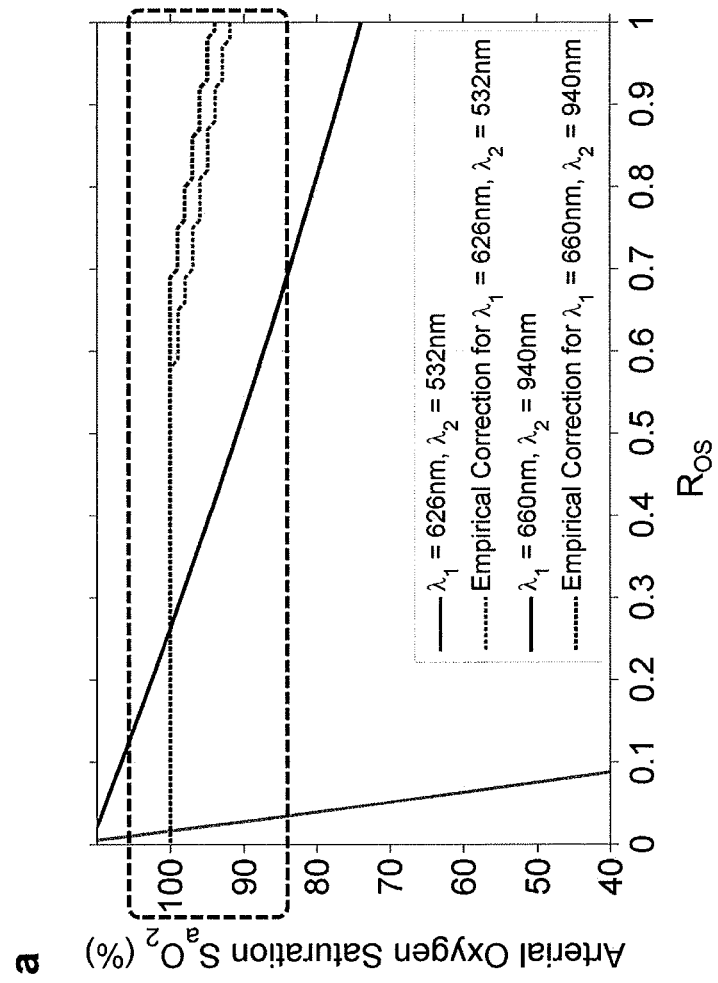

FIG. 12A shows arterial oxygen saturation ($S_aO_2$) as a function of transmitted light ratio ($R_{OS}$); the black solid line shows the curve generated by Beer-Lambert's Law for red ($\lambda$=660 nm) and infrared ($\lambda$=940 nm) light. Similarly, the green solid line shows the curve generated by Beer-Lambert's Law for red ($\lambda$=626 nm) and green ($\lambda$=532 nm) light. Calibration curves to overcome limitations of Beer-Lambert's Law in scattering tissue (versus a glass cuvette) are shown by dashed lines. $R_{OS}$ values were measured for various $S_aO_2$ values.

Figure 12B:
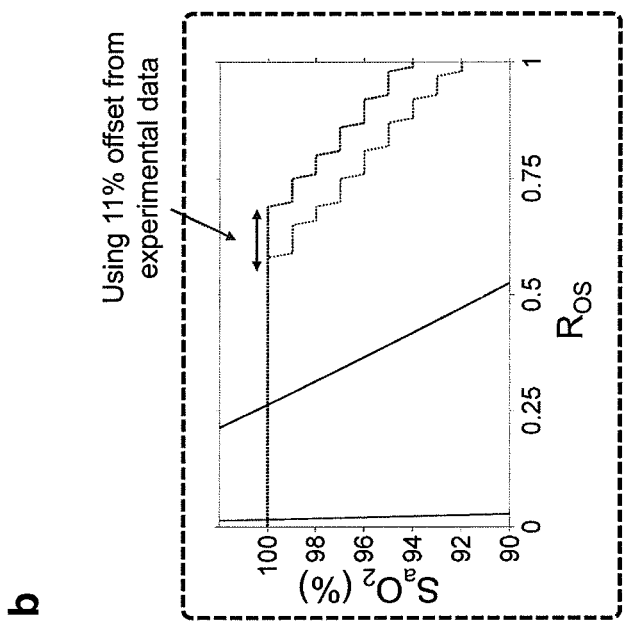

FIG. 12B shows an observed 11% offset for the green light oximeter (green dashed line) from the conventional oximeter (black dashed line).

Figure 13A:
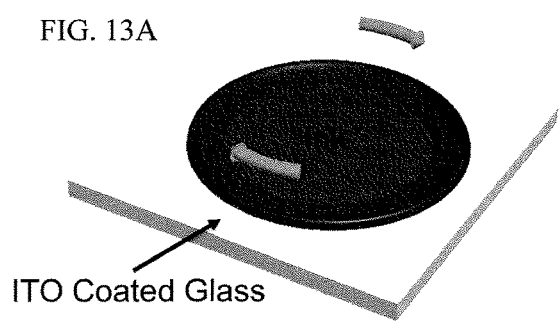

FIG. 13A shows OLED and OPD fabrication and physical device structures with OLEDs fabricated on a glass substrate using spin coating according to an embodiment. FIG. 13C shows the OPDs fabricated using blade coating on a PEN substrate according to an embodiment.

Figure 13B:
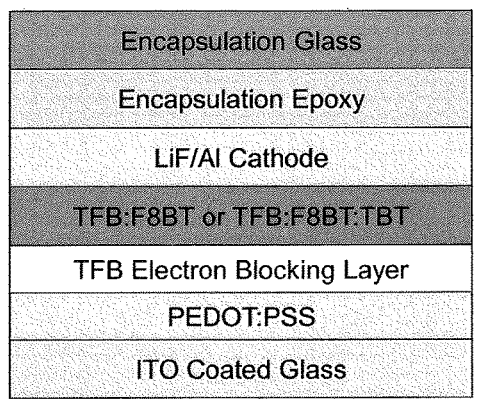
Figure 13C:
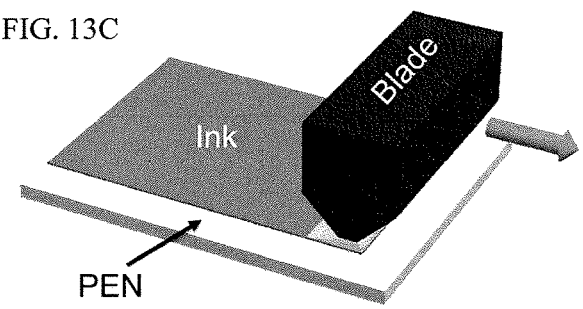
Figure 13D:
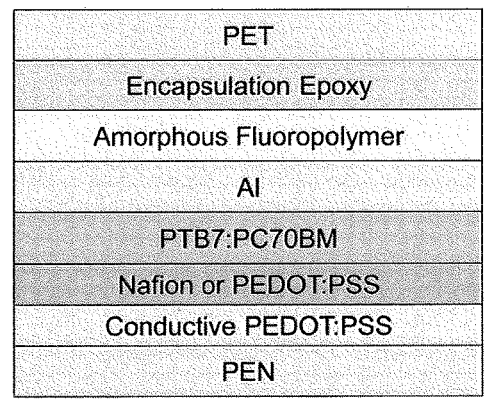

FIGS. 13B and 13D respectively show the physical structures of the OLEDs and OPDs according to embodiments.

Figure 14B:
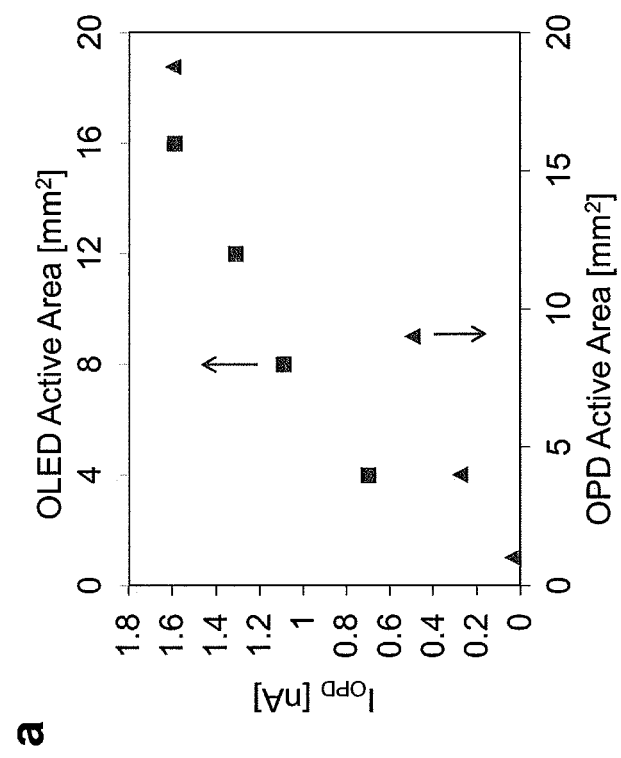
Figure 14A:
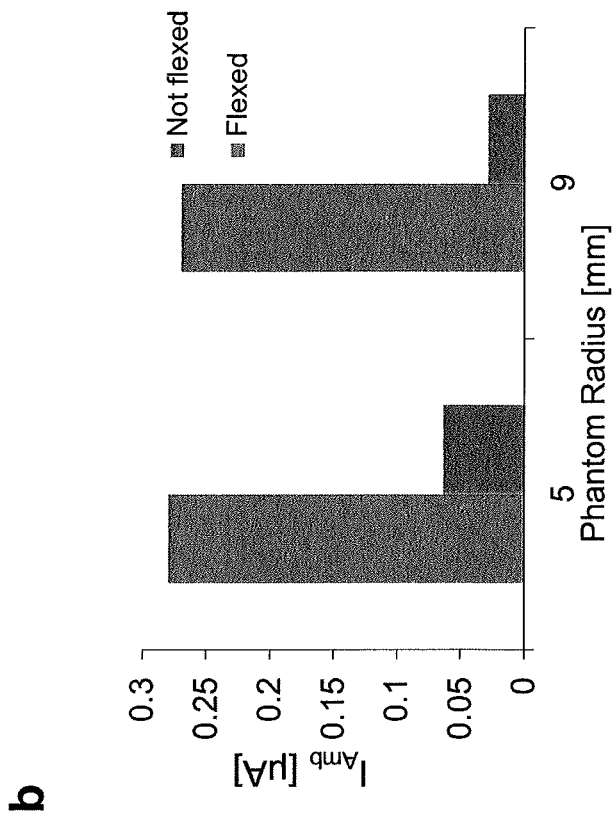

FIG. 14A shows area scaling effects of OLEDs and OPDs, and reducing ambient noise by flexing the OPD around a finger phantom; OPD current ($I_{OPD}$) was observed for different OLED and OPD active areas, where higher photocurrent resulted with area scaling of the OLEDs and OPDs.

FIG. 14B shows OPDs flexed around 5 mm and 9 mm radius phantoms representative of small and large human fingers; 79% and 93% reduction in ambient noise were observed for the OPDs flexed around the phantoms, respectively.

Figure 15:
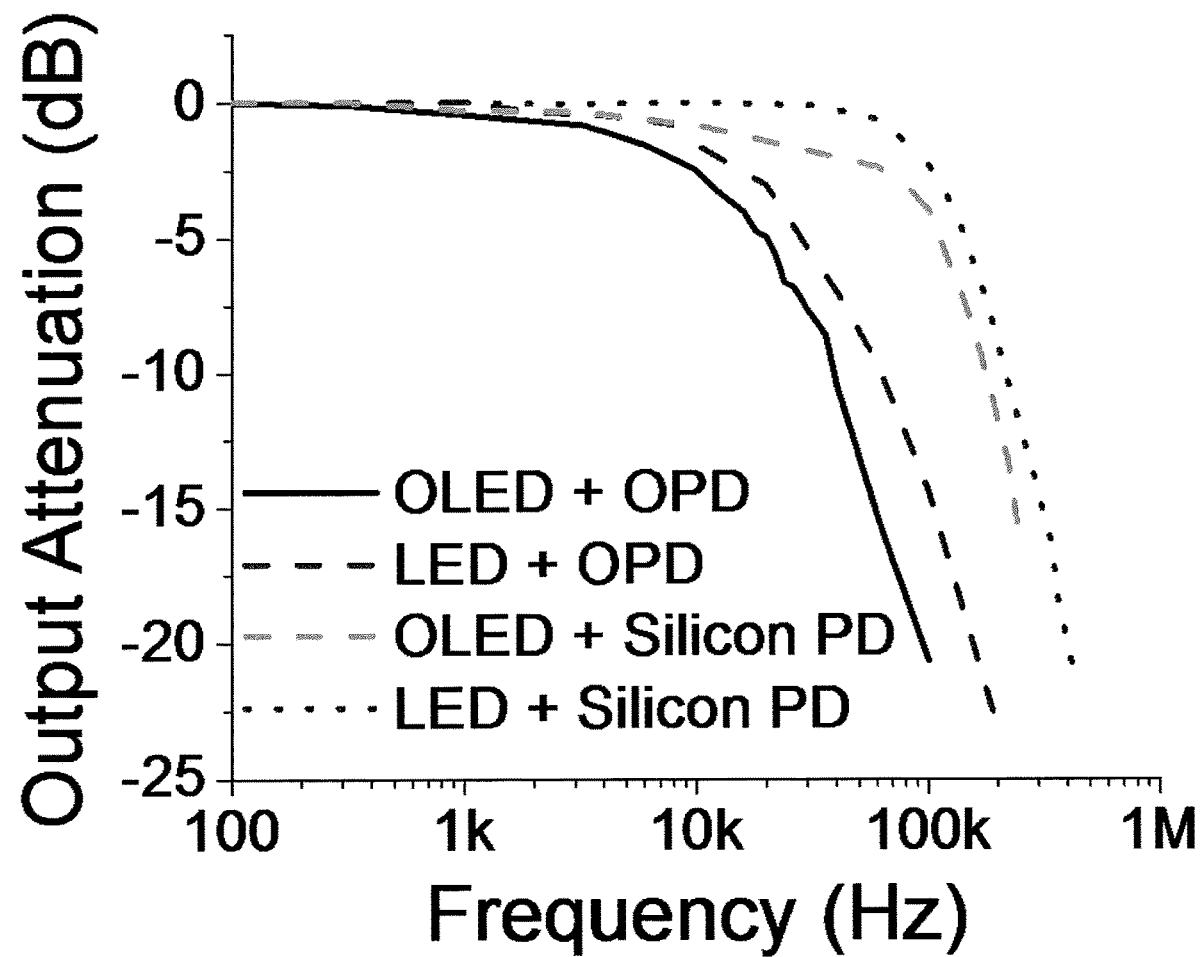

FIG. 15 shows frequency response of various organic and inorganic LED and PD configurations; the inorganic LED and PD showed the best response with a 3 dB cutoff greater than 100 KHz. For the all organic combination with OLED and OPD, a 10 KHz cutoff was obtained, which is significantly higher than the 1 KHz operation of the oximeter. Green ($\lambda$=532 nm) LEDs and OLEDs were used with a 5 V peak to peak sinusoidal signal and a DC offset of 2.5V.

DETAILED DESCRIPTION

The present disclosure provides systems and methods to measure pulse and blood oxygen saturation in humans using reflectance spectroscopy. In certain embodiments, the systems and methods use solution processed Light Emitting Diodes (LEDs), such as organic light emitting diodes (OLED s) and solution processed photodetectors, such as organic polymer photodiodes (OPDs). Two different wavelengths of light (e.g., red and green, or red and infrared) illuminate, or are input onto, an area of human tissue by the OLEDs, and reflected light is recorded by the organic photodetector. The light emitting elements and the sensor or detector element(s) can be positioned on opposite sides of the tissue and traditional transmission measurements made, albeit with red and green light, or the light emitting elements and the detector element(s) can be positioned on the same side of the tissue where the reflection measurements are made.

Figure 1:
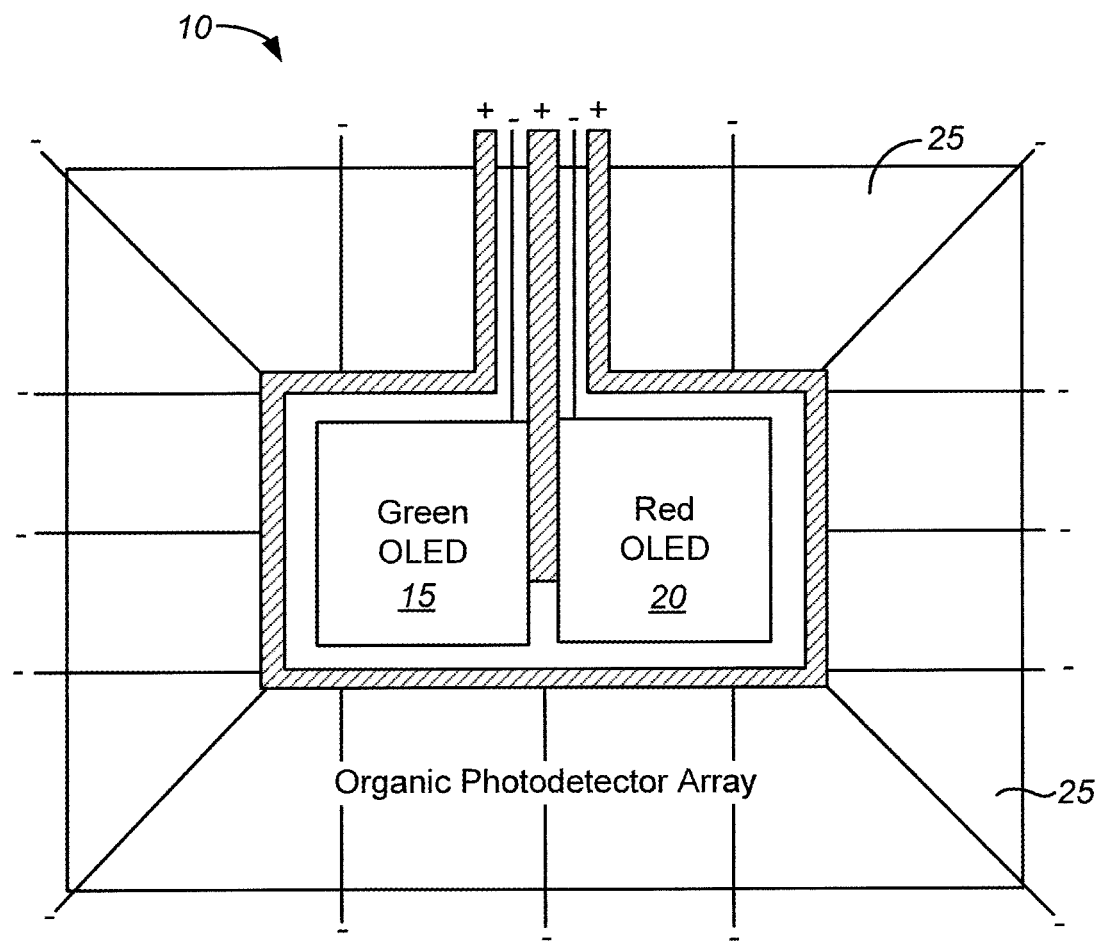
FIG. 1 shows an example of a blood oximeter including a green OLED and a red OLED according to an embodiment.
Figure 2:
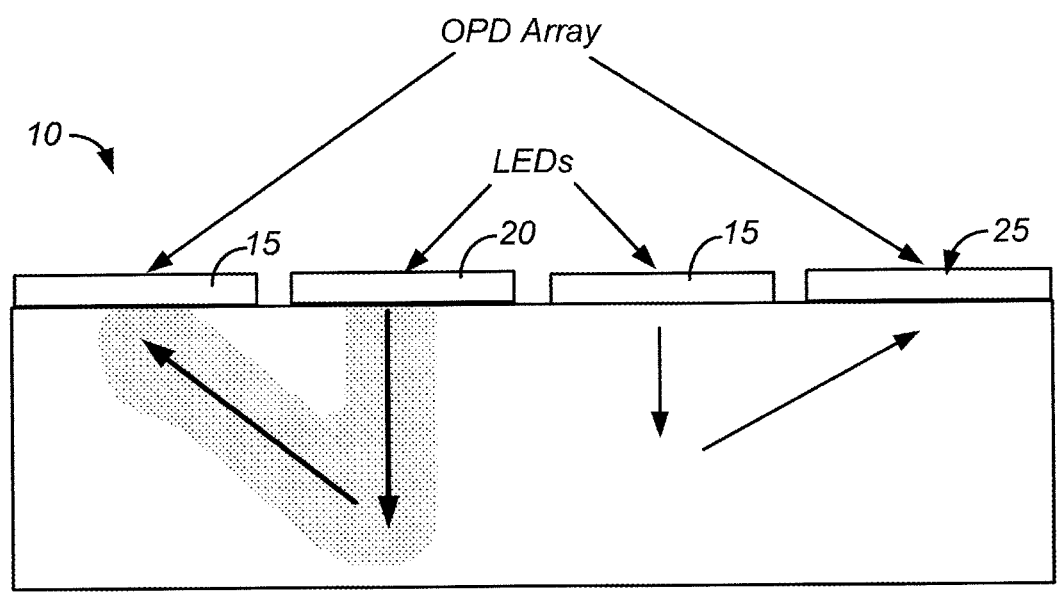
FIG. 2 shows a side view of the oximeter of FIG. 1.

According to one embodiment, an oximeter device includes a first light emitting element that emits red light, a second light emitting element that emits green light, and a sensor element that detects red and green light and that outputs signals representing detected red and green light. FIG. 1 shows an example of a blood oximeter device 10 including a green OLED 15 and a red OLED 20 according to an embodiment. Device 10 includes at least one photodetector, and may include an array of multiple photodetectors 25 as shown. The array of photodetectors 25 may include multiple photodetectors 25 spaced equally around the OLED elements, or the photodetectors may be spaced irregularly around the LEDs. FIG. 2 shows a side view of the oximeter device 10 of FIG. 1.

In certain embodiments, a pulse oximeter device 10 includes arrays of OLEDs and OPDs. For example, in one embodiment, pulse oximeter device 10 includes a plurality of first light emitting elements 20 that emit red light, a plurality of second light emitting elements 15 that emit green light, and a plurality of sensor elements 25 that detects red and green light and that output signals representing detected red and green light.

According to one embodiment, the organic LED portion of the system includes at least two polymer LEDs (PLEDs), at least one emitting red light (e.g., 626 nm) and at least one other emitting green light (e.g., 530 nm). In one embodiment, a red PLED is made from a blend of poly(9,9-dioctylfluorene-co-n-(4-butylphenyl)-diphenylamine) (TFB), poly [(9,9-di-n-octylfluorenyl-2,7-diyl)-alt-(benzo[2,1,3] thiadiazol-4,8-diyi)] (F8BT), and poly((9,9-dioctylfluorenyl-2,7-diyl)-alt-(4,7-bis(3-hexylthiophen-5-yl)-2,1,3-benzothiadiazole)-2',2"-diyl) (TBT). The TFB, F8BT, and TBT components of the blend are mixed in a 25:70:5 ratio with a 10 mg/mL concentration in o-xylene. A green PLED is made from a blend of TFB and F8BT with a 1:9 ratio and 10 mg/mL concentration in o-xylene.

Organic photodiodes (OPDs) are used to detect or sense the reflected PLED light signal. Examples of two materials that may be used include: Poly({4,8-bis[(2-ethylhexyl)oxy] benzo[1,2-b:4,5-b']dithiophene-2,6-diyl}{3-fluoro-2-[(2-ethylhexyl)carbonyl]thieno[3,4-b]thiophenediyl}) (PTB7) is used for sensing visible wavelengths whereas as a boron-dipyrromethene (BODIPY)-based polymer is used for sensing visible and near infrared (NIR) wavelengths beyond 750 nm. PTB7 is mixed with phenyl-C 70-butyric acid methyl ester (PC70BM) to a 1:1 weight ratio in chlorobenzene with additive concentrations of 1,8 diodooctane. The BODIPY-based polymer is mixed with phenyl-C 70-butyric acid methyl ester (PC70BM) to a 1:2 weight ratio in 1,2 dichlorobenzene.

Figure 3:
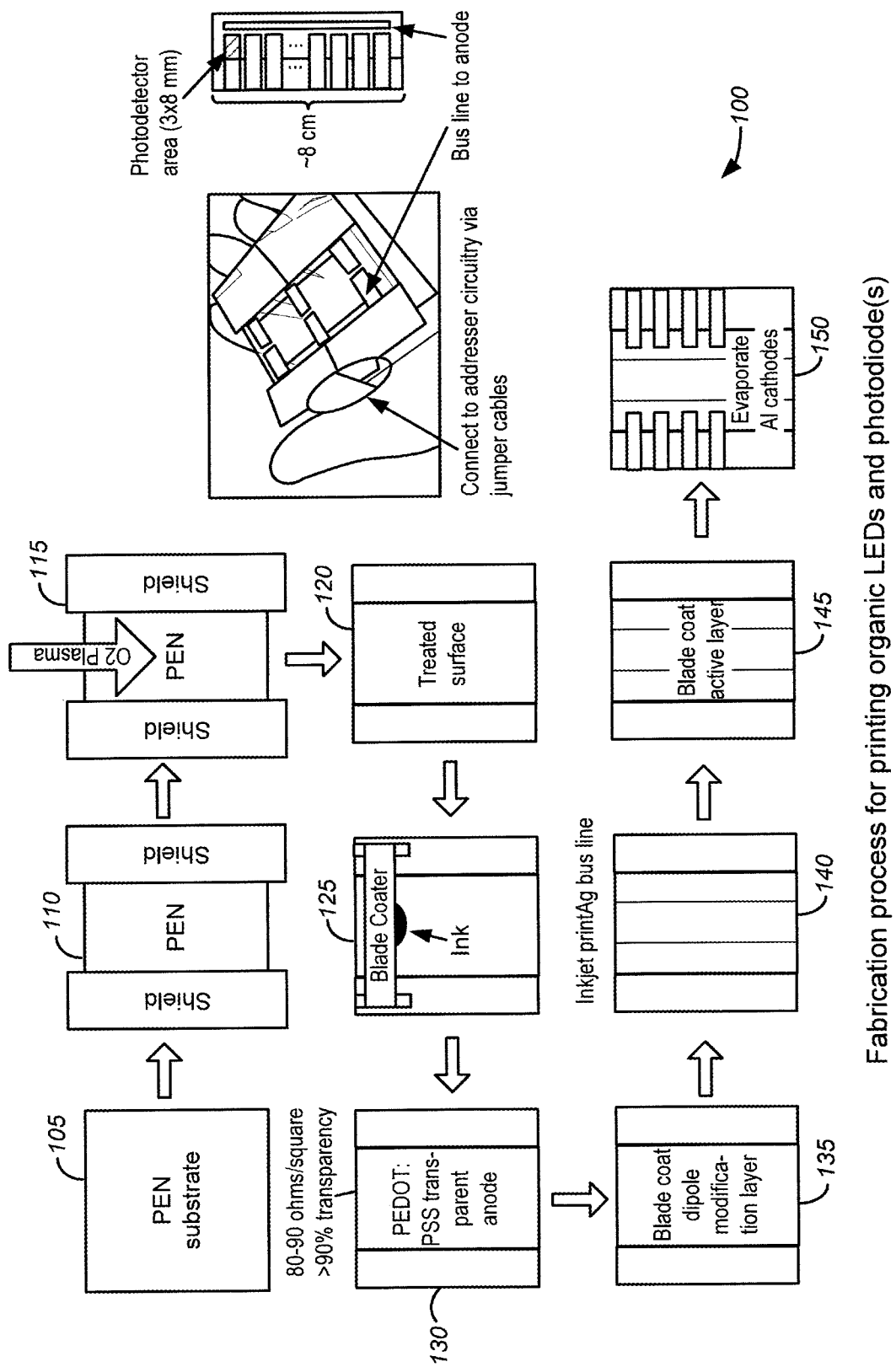
FIG. 3 shows an example process for forming an oximeter device according to an embodiment.

FIG. 3 shows an example process 100 for forming an oximeter device according to an embodiment. In certain embodiments, both PLED and OPD devices are fabricated on a substrate material, which in one embodiment includes a polyethylene naphthalate (PEN) substrate (105). Other useful substrate materials might include polyethylene terephthalate (PET). At step 110, a mask is used to cover the edges of the substrate during an $O_2$ plasma treatment at step 115, rendering the un-covered portion of the substrate hydrophilic (120). A highly conductive formulation, such as a poly(3,4-ethylenedioxythiophene) poly(styrenesulfonate) (PEDOT:PSS) formulation, is doctor bladed over the substrate at step 125, only coating the hydrophilic portion. At step 130, a layer of high work function material, e.g., PEDOT:PSS, is doctor bladed over the conductive PEDOT: PSS to increase the work function of the anode. Bus lines, e.g., Ag lines are printed at step 140. Following this, at step 145, the active layers of the aforementioned PLED and OPD devices are doctor bladed. At step 150, cathodes are formed, e.g., lithium fluoride (LiF) and aluminum (Al) are thermally evaporated through a metal stencil to form the cathode. The pixels of the cathode are arranged in a linear array and are connected to external circuitry with the use of flat flexible cables (FFCs) bonded to the substrate mechanically or with anisotropic conductive film (ACF).

In order to eliminate cross-talk between the PLEDs and OPD array, a vertical (or horizontal) polarizing sheet is adhered to the PLEDs and a horizontal (or vertical) polarizing sheet is adhered to the OPD array in certain embodiments, ensuring only light reflected from the body will contribute to the OPD signal.

In certain embodiments, organic light emitting diodes may be spin-coated or blade-coated to form a reflectance pulse oximeter as described herein. For example, a spin-coated organic light emitting diode may be fabricated according to one exemplary embodiment as follows:

1. A substrate, e.g., ITO-coated substrate (glass or plastic), is cleaned via subsequent sonication in soapy DI water, water, acetone, and IPA. The substrate is then dried with N2 between each step.
2. The substrate is treated via UV-Ozone or Plasma treatment.
3. The hole injection layer (e.g., filtered PEDOT:PSS AI4083) is spin-coated onto the substrate to form a thick (e.g., from about 40 nm to about 100 nm) layer.
4. The device is plasma treated (e.g., for 5-8 s) in order to improve the wetting of the PEDOT:PSS layer.
5. The electron blocking layer (e.g., polymer such as TFB) is spin-coated from solution to form a layer (e.g., from about 10-15 nm thick).
6. The electron blocking layer is annealed above its glass transition temperature, e.g., for about 1 hour.
7. The electron blocking layer is rinsed, e.g., by spinning a solvent on it using a spin coater.
8. The electroluminescent polymer solution is spin-coated onto the electron blocking layer to form a thick (e.g., on the order of 100 nm or so) film.
9. A Ca/Al or LiF/Al cathode is evaporated.
10. A UV-curable epoxy and encapsulating glass or plastic is applied to the finished device.

Blade-coated organic light emitting diodes may be fabricated according to exemplary embodiments as follows:

A. Top-emission organic light emitting diodes:
1. The substrate (plastic) is cleaned via sonication in IPA.
2. A chromium adhesion layer (e.g., on the order of about 5 nm) is thermally evaporated onto the substrate.
3. A silver anode layer (e.g., on the order of about 100 nm) is thermally evaporated onto the chromium adhesion layer.
4. The Ag anode may or may not be patterned with a nanometer scale hole array in order to improve the device efficiency by scattering surface plasmon polaritons back into the device instead of allowing them to dissipate into heat on the anode.
5. A mixture of PEDOT:PSS and zonyl surfactant hole injection layer is blade coated onto the silver layer to form a thick film (e.g., on the order of about 100 nm).
6. The device is plasma treated (e.g., for 5-8 s) in order to improve the wetting of the PEDOT:PSS layer
7. The electron blocking layer (polymer such as TFB) is blade coated from solution to form a thick film (e.g., on the order of about 10 to 15 nm).
8. The electron blocking layer is annealed above its glass transition temperature, e.g., for about 1 hour.
9. The electron blocking layer is rinsed by blade coating the solvent over it.
10. The electroluminescent polymer solution is blade-coated to form a thick film (e.g., on the order of about 100 nm) over the electron blocking layer.
11. A thin and optically transparent Ca/Al or LiF/Al cathode is evaporated onto the device. A thin and optically transparent Ag layer may be evaporated on top of the Al layer in order to enhance the conductivity of the electrode. The thickness of each cathode layer may be optimized to enhance the microcavity effect in the device in order to narrow the full-width half maximum of the electroluminescence spectrum. A dielectric material may also be evaporated over the cathode in order to achieve the desired microcavity effect.
12. A flexible UV-curable epoxy and encapsulating plastic is applied to the finished device.

B. Bottom-emission organic light emitting diodes:
1. The ITO coated plastic substrate is cleaned via sonication in IPA.
2. PEDOT:PSS AI4083 is blade coated to form a thick film (e.g., on the order of about 100 nm).
3. The device is plasma treated, e.g., for 5-8 s, in order to improve the wetting of the PEDOT:PSS layer
4. The electron blocking layer (polymer such as TFB) is blade coated from solution to form a thick film (e.g., on the order of about 10 to 15 nm).
5. The electron blocking layer is annealed above its glass transition temperature, e.g., for about 1 hour.
6. The electron blocking layer is rinsed by blade coating the solvent over it.
7. The electroluminescent polymer solution is blade-coated to form a thick film (e.g., on the order of about 100 nm) over the electron blocking layer.
8. A Ca/Al or LiF/Al cathode is evaporated onto the device.
9. A flexible UV-curable epoxy and encapsulating plastic is applied to the finished device.

Figure 4:
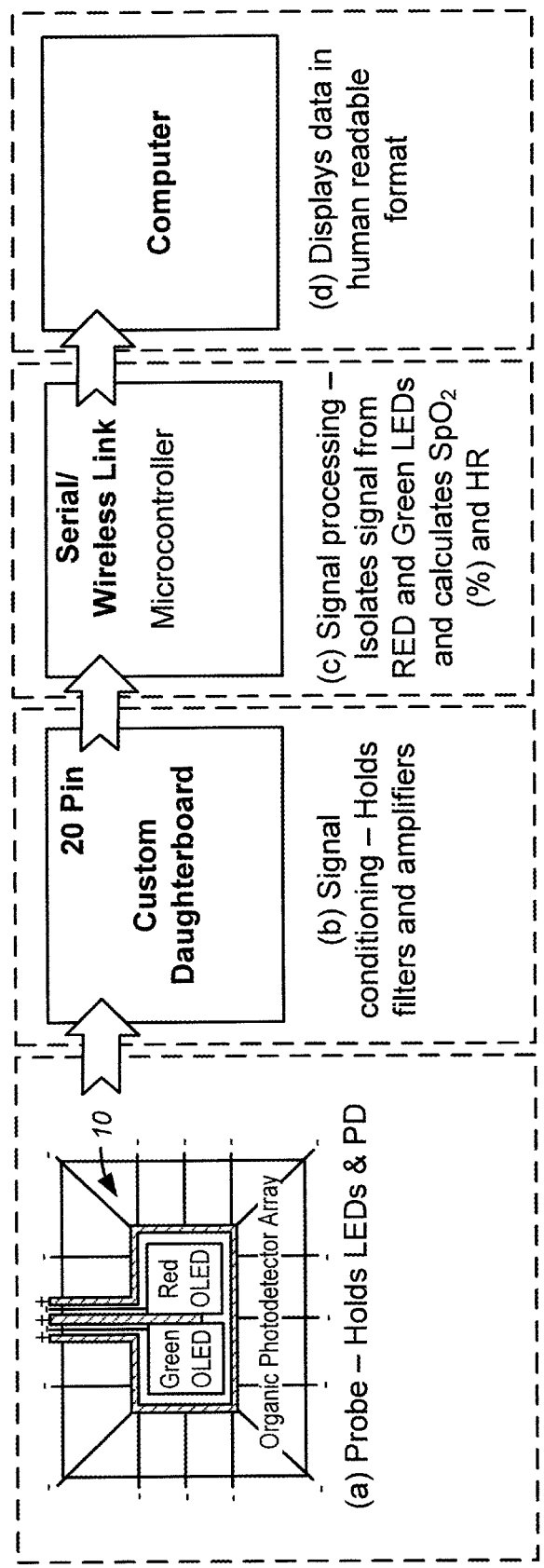
FIG. 4 illustrates a system level overview of an oximeter design according to an embodiment.

FIG. 4 illustrates a system level overview of an oximeter design according to an embodiment. A compact and modular circuit composed of a Texas Instruments MSP430 microcontroller is utilized in one design for reliable data collection and processing. The system is devised in a segmented approach: including (a) driver circuit for organic LEDs, (b) data read circuit for organic photodetector, and (c) data processing circuit for computing blood oxygen saturation and transmitting results to a computer or output device. Digital to analog converter (DAC) of the microcontroller is used to control light intensities of the organic LEDs, and an analog to digital converter (ADC) is used to read data from the organic photodetector. A drive circuit (e.g., 9 V LED drive circuit) modulates the red and the green LEDs, and multiple (e.g., 512) samples are taken from each of the LEDs in a second with a data read circuit for the organic photodetector. Blood oxygen saturation is then calculated by analyzing data from the organic photodetector. Raw signal from the photodetector is filtered and amplified to ensure signal integrity. Filters and amplifiers are part of the main circuit block. The complete system is optimized for OLEDs and OPD—a voltage shift circuit shifts signal level to 9V to operate the OLEDs. Additionally, the system is realized on a flexible printed circuit board (PCB), which improves the versatility of the system. The printed organic LEDs (OLEDs) and photodetector (OPD) for pulse oximetry can be used to monitor the pulse and respiratory health of medical patients (for both in-hospital and at-home monitoring), military high-altitude aircraft pilots, mountain climbers and others.

The flexibility of the sensor system also allows oximetry to be utilized to diagnose and alert medical care professionals to the development of bed sores on hospital patients and bed-ridden nursing home residents. An array of OLEDs and OPDs can be incorporated into a patch that can be adhered to the skin, e.g., of people at-risk for bed sore development. If the oxygen saturation of the tissue covered by the patch drops below the average value, the person's caretaker is notified by external circuitry attached to the patch and the body can be re-positioned to prevent the full formation of the bed sore. Similarly, the sensor system could be used to monitor oxygenation of skin around wounds. Doctors could use this data to infer how well the wound may be healing.

In one embodiment, a method of measuring blood oxygenation content of a tissue sample, comprises applying a flexible pulse oximeter device proximal the tissue sample, wherein the pulse oximeter device includes a flexible substrate, at least one first light emitting element formed on the substrate that emits red light, at least one second light emitting element formed on the substrate that emits green light, and at least one sensor element formed on the substrate that detects red and green light and that outputs signals representing detected red and green light. The method also typically includes activating the at least one first light emitting element and the at least one second light emitting element, detecting red and green light reflected by the tissue by the at least one sensor element, and outputting signals representing the detected reflected red and green light to a signal processing device.

In certain embodiments, the systems and devices of the present disclosure are useful for mapping blood oxygenation of regions of a tissue sample containing blood, e.g., regions of a patient's skin. For example, in one embodiment, a method of mapping blood oxygenation content of a region of a tissue sample includes applying a flexible pulse oximeter device proximal the tissue sample, wherein the pulse oximeter device includes a flexible substrate, an array of first light emitting elements formed on the substrate that emit red light, an array of second light emitting elements formed on the substrate that emit green light, and an array of sensor elements formed on the substrate that detect red and green light and that output signals representing detected red and green light. The method also typically includes activating a first portion of the array of first light emitting elements and a first portion of the array of second light emitting element, detecting red and green light reflected by the tissue by a first sensor element, and outputting signals representing the detected reflected red and green light to a signal processing device. The data and signals received and processed may be stored to a memory device or unit. The method further typically includes repeating steps of activating, detecting and outputting for a second portion of the array of first light emitting elements, second light emitting elements and a second sensor element. In certain aspects, the steps of repeating can occur simultaneously with the initial steps of activating, detecting and outputting, or can occur after the steps of activating, detecting and outputting.

Current blood oximeter technology is limited by the inflexibility of the sensor component: measurements can only be reliably taken from finger or earlobe test sites and are sensitive to motion. By creating a printed sensor on a flexible substrate that can make reflectance measurements as opposed to only transmission measurements, new applications for blood oximetry advantageously become available. The printed sensor can easily be fabricated in a variety of sizes, allowing for blood oxygenation monitoring on virtually any part of the body with blood flow. This will make oximetry a viable monitoring tool for bed sore development and wound healing, alongside standard respiratory health.

The oximeter devices of the present disclosure can be used to monitor blood oxygen saturation levels via reflectance measurements in a wide variety of body locations due to the flexible nature of the sensor. Examples of applications of the pulse oximeter devices of the present disclosure include:

1. Diabetes monitoring: Monitor blood circulation in limbs of diabetic patients.
2. Reconstructive surgery monitoring: Monitor circulation and oxygenation of skin flap transplant.
3. Pressure ulcer monitoring: Monitor circulation and oxygenation of tissue at risk for pressure ulcer formation.
4. Daily health monitoring: Monitor pulse and arterial blood oxygenation from the wrist.

Advantages of the oximeters of the present disclosure compared with current blood oximeters is that they can be used on more body locations than the finger or ear because they are flexible and can take reflectance based measurements instead of only transmission based measurements. The present oximeters can also be inexpensively made and are disposable compared to the current technology.

The flexible printed sensor portion of the blood oximeter is electrically connected to the power supply, driver, data read, and data processing portion of the device. The sensor is encapsulated in a sanitary and transparent FDA-approved cling film outer layer before it is adhered to a subject's body with an FDA-approved adhesive. Once secure contact is made to the body, the device will be turned on and begin to make reflectance measurements. Data will be processed by standard processing equipment in order to calculate and display the blood oxygen saturation value.

In one embodiment, an oximeter includes a reconfigurable arrangement of photodiodes, LEDs, biopotential electrodes, and interconnects printed on a flexible, conformal substrate at very low cost, coupled to a robust wireless interface and software platform. A fully flexible, fully conformable pulse oximetry and biopotential sensors with minimal external circuitry to facilitate continuous, wireless transmission of oxygenation saturation from currently inaccessible areas. FIG. 4 shows a system level overview of an oximeter design according to an embodiment: (a) Oximeter probe acquires raw signal using the organic LEDs and photodetector, (b) the signals from the Photodetector array are averaged with an adder into one signal which is then filtered and amplified to ensure signal integrity, (c) thereafter, blood oxygen saturation is computed by comparing data from the red and green LEDs acquired by the photodetector, (d) results are sent to the computer via a serial/wireless link.

Figure 5:
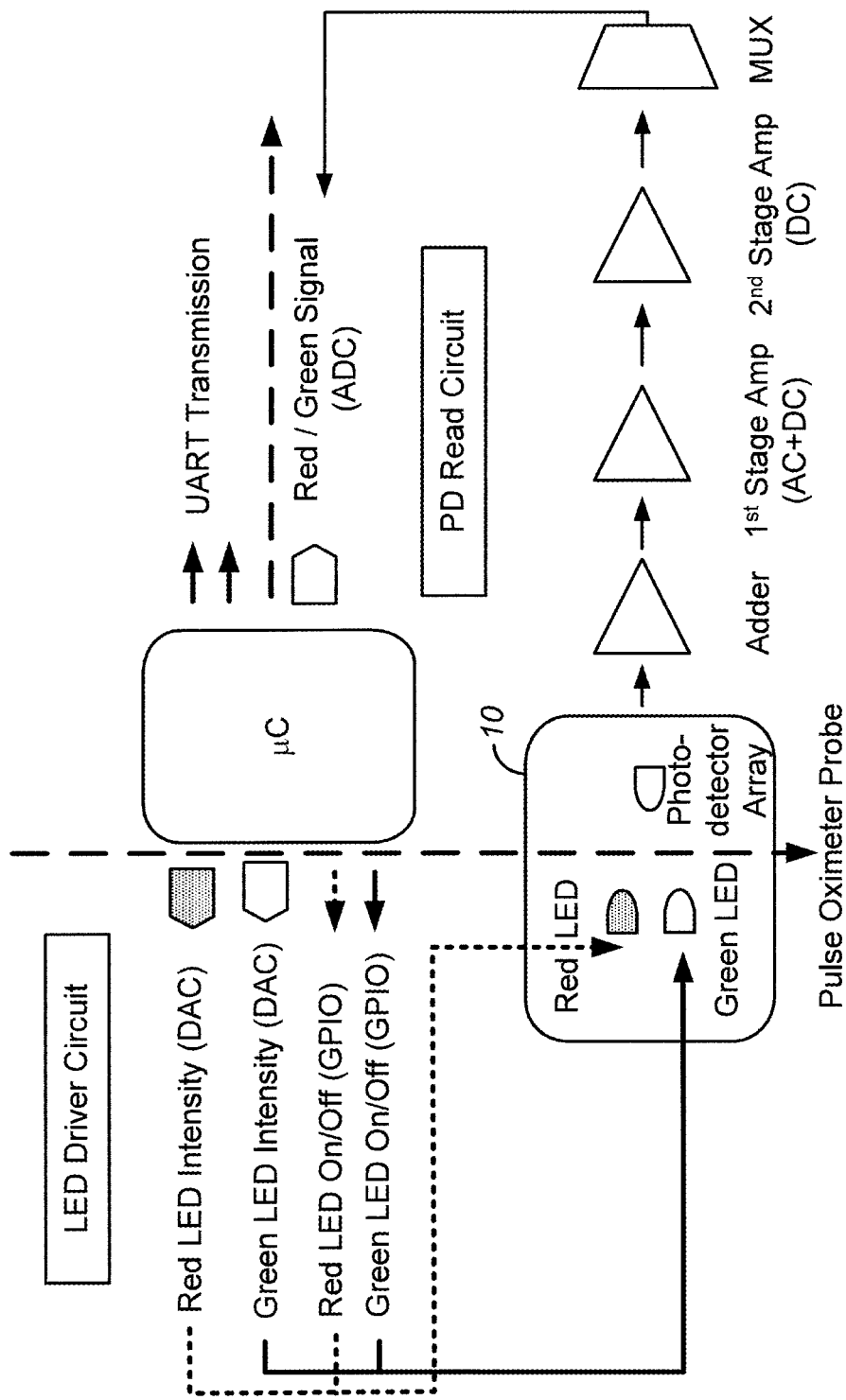
FIG. 5 shows a cross-sectional view of an example of pulse oximeter device according to an embodiment.

A configurable array of conformable optoelectronics is provided in certain device embodiments. For example, a sensor board uses flexible printed components, and the analog front-end and processing board uses solid-state components. The sensors are printed on a flexible substrate. Printed gold traces connect the components to a control board. The control board hosts the driver electronics for driving the OLEDs and reading OPD current signals. The sensor board is interfaced with a polyimide flex board that hosts solid-state electronic components for data processing and transmission. The control board utilizes a Bluetooth 4.0 compatible microcontroller, antenna, battery, and optional external memory. The sensor board is connected with the polyimide control board using anisotropic conductive film (ACF) or low temperature solder bonding (depicted in FIG. 5). In this manner, the microcontroller and wireless chips can be used for data processing and data transmission. FIG. 5 shows a cross-sectional view of an example of pulse oximeter device according to an embodiment. The polyimide flex circuit board (yellow board) is connected to the sensor board (blue board) by routing out signals from the flex board and then ACF/low temperature solder bonded to the sensor board pads. Where the sensor design is application specific, the polyimide circuit and rigid components on it need not be attached to the back of the plastic sensor—optimum location can be varied depending on the application.

Leveraging the recent advances in flexible and solution-based electronics, the flexible and wearable sensor board is composed of a printed electrode array capable of measuring biopotential/bioimpedance and electrical routing for integrating sensors. The primary sensor is a pulse oximeter "pixel", which is utilized to sense oxygen saturation. The pixel is composed of two organic light emitting diodes (OLEDs) and a large area organic photodiodes (OPD) with a configurable number of pixels. Certain embodiments will have arrays of pixels. The arrangement of the OLEDs and OPD pixels maximizes reflected light collection. The biopotential electrodes, an additional sensing modality, are placed at the periphery of the board. These connections are routed to a multiplexer, and the control circuit can extract specific pairs for reading signal. Electrical connections from the sensors are routed to standard flat flex cable (FFC) pads. Since the optoelectronics and biopotential electrodes are printed, pixel and biopotential electrode placement can be optimized for a particular clinical application.

Figure 6:
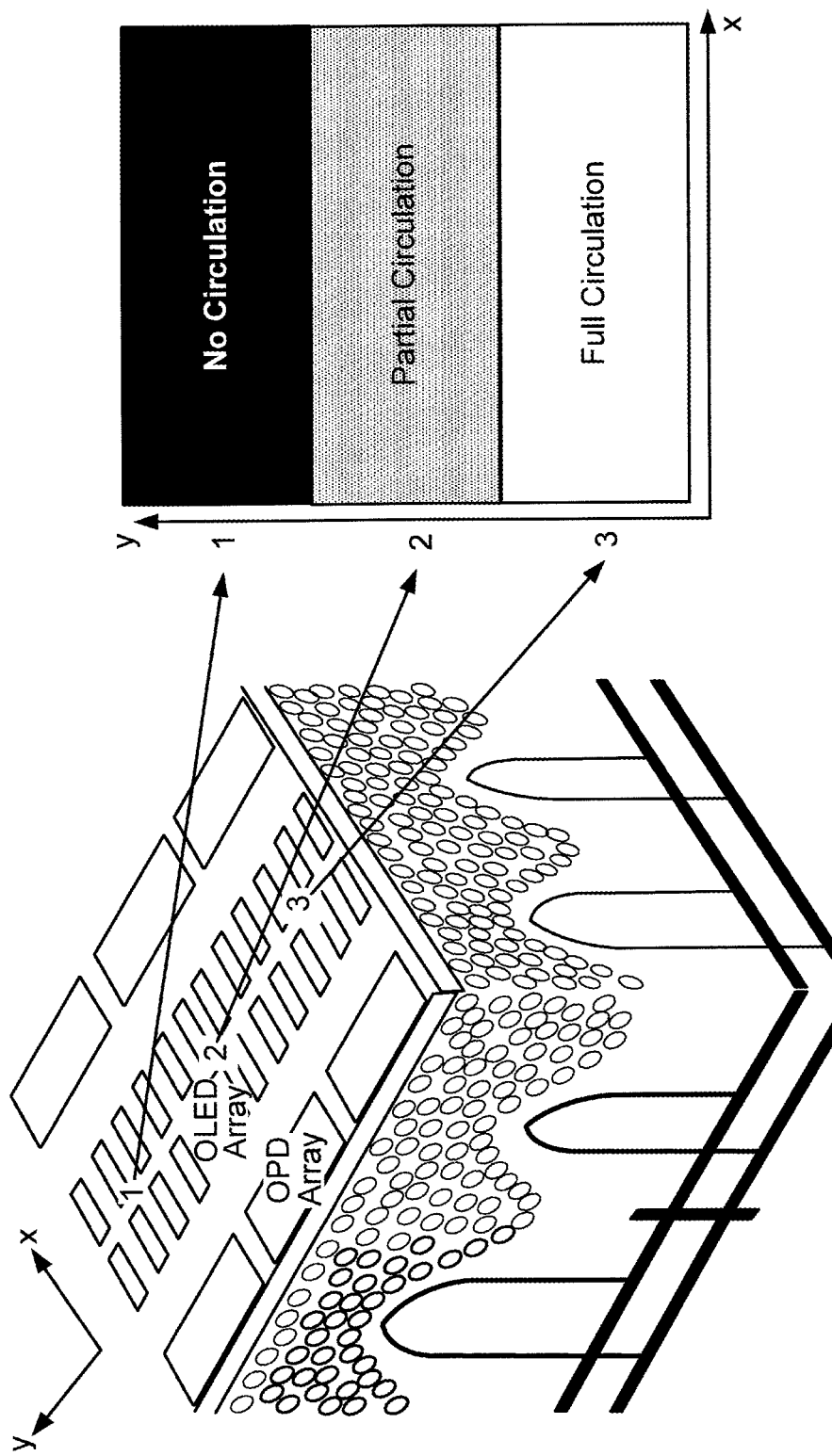
FIG. 6 illustrates an example of a pulse oximeter device, including an array of elements, applied to an epidermal structure (e.g., subject's skin) according to an embodiment.

FIG. 6 illustrates an example of a pulse oximeter device, including an array of elements, applied to an epidermal structure (e.g., subject's skin). The array of red and green OLEDs and OPDs is used to take a 2-D measurement of blood circulation via reflectance oximetry. The reflectance oximeter is able to sense areas of blood circulation vs. non-circulation. Area 1 shows skin cells and capillaries not receiving circulation. Area 2 senses an area where there is partial circulation. Area 3 senses an area with full blood circulation. In areas with full blood circulation, pulse and arterial blood oxygenation can also be measured.

Noninvasive pulse oximetry is a ubiquitous medical sensing method for measuring pulse rate and arterial blood oxygenation. Conventional pulse oximeters use expensive optoelectronic components that restrict sensing locations to finger tips or ear lobes due to their rigid form and area scaling complexity. Advancement in flexible electronics could lead to improvements in oxygenation monitoring by allowing ubiquitous placement of wearable sensors on the human body. In this work, a pulse oximeter sensor based on organic materials, compatible with flexible substrates, capable of measuring heart rate and arterial oxygen saturation is disclosed. Green (532 nm) and red (626 nm) organic light emitting diodes (OLEDs) were used with an organic photodiode (OPD) sensitive at the aforementioned wavelengths. The sensor's active layers were deposited from solution-processed materials via spin coating and printing techniques. The all organic optoelectronic oximeter sensor was interfaced with conventional electronics at 1 KHz to provide accurate pulse and blood oxygenation measurements. The acquired pulse rate and oxygenation were calibrated and compared to a commercially available oximeter; a 1% error in pulse rate measurements and 2% error in the oxygenation measurement were found.

Conventional pulse oximeters non-invasively measure human pulse rate and arterial blood oxygen saturation with an optoelectronic sensor composed of two inorganic light-emitting-diodes (LEDs) with different peak emission wavelengths and a single inorganic photodiode. The LEDs are placed on one side of a finger and the light transmitted through the tissue is subsequently sensed by the photodiode which is placed on the opposite side of the finger. Sequential sampling of the transmitted light provides information on the ratio of oxygenated and deoxygenated hemoglobin in the blood. This ratio and a calibration curve are used to compute arterial blood oxygen saturation. Currently, the application of commercially available pulse oximeters is limited by the bulk, rigidity, and high large-area scaling cost of conventional inorganic based optoelectronics. Here a pulse oximeter sensor composed of organic polymer light emitting diodes (OLEDs) and a flexible organic polymer photodiode (OPD) is disclosed. The organic optoelectronic sensor provides accurate measurement capability, and application of such solution processable organic optoelectronics in pulse oximetry will enable low-cost, disposable, and wearable medical devices.

Wearable medical sensors have the potential to play an essential role in the reduction of health care costs: they encourage healthy living by providing individuals feedback on personal vital signs and enable the facile implementation of both in-hospital and in-home professional health monitoring. Consequently, wide implementation of these sensors can reduce prolonged hospital stays and cut avertible costs. Recent reports show ample wearable sensors capable of measuring pressure, biopotential and bioimpedance, pulse rate, and temperature in real time. These sensors are developed in wearable and flexible form-factors using organic, inorganic, and hybrid organic-inorganic materials.

OLEDs and OPDs have been developed primarily for use in displays and photovoltaics applications due to the potential of using additive solution processing, which enables inexpensive roll-to-roll manufacturing, large area, and large volumes scalability. These same manufacturing properties make OLEDs and OPDs attractive candidates for medical sensors. In addition to economically viable large-area sensors manufacturing, the mechanical flexibility that is achieved with organic optoelectronic devices offers a conformal fit around the human body, resulting in an improvement of the overall sensor performance. Organic optoelectronics have previously been used to perform pulse measurements. Here, though, a sensor composed solely of organic optoelectronics that measures both human pulse and arterial blood oxygenation is provided. A schematic view of the sensor is given in FIG. 7A, where two OLED arrays and one OPD are placed on opposite sides of a finger.

Pulse and Oxygenation With Red and Green Light Emitting Diodes:

In contrast to commercially available inorganic oximetry sensors, which use red and near-infrared LEDs, red and green OLEDs are included in the present device. Incident light from the OLEDs is attenuated by pulsating arterial blood, non-pulsating arterial blood, venous blood, and other tissue as depicted in FIG. 7B. When sampled with the OPD, the transmitted light peaks in diastole (the heart's relaxation phase) and reaches a minimum during systole (the heart's contraction phase), which translates to a pulsatile, AC, signal—the human pulse. The DC signal resulting from the nonpulsating arterial blood, venous blood, and other tissue, is subtracted from the pulsating signal to give the amount of light absorbed by the oxygenated and deoxygenated hemoglobin in the pulsating arterial blood. Oxyhemoglobin ($HbO_2$) and deoxyhemoglobin (Hb) have different absorptivities at red and green wavelengths, as highlighted on the absorptivity of oxygenated and deoxygenated hemoglobin plotted in FIG. 7C. The difference in the molar extinction coefficient of oxygenated and deoxygenated hemoglobin at the green wavelength is comparable to the difference at near-infrared wavelengths (800-1000 nm) used in conventional pulse oximeters. In addition, solution-processable near-infrared OLED materials are not stable in air and show overall lower efficiencies. Thus green OLEDs are used instead of near-infrared OLEDs in certain embodiments.

Using red and green OLEDs and an OPD sensitive at visible wavelengths (the OLEDs' emission spectra and the OPD's external quantum efficiency (EQE) as a function of incident light wavelength are plotted in FIG. 7D), blood oxygen saturation ($SO_2$) is quantified according to Eq. 1. Here, $C_{HbO_2}$ and $C_{Hb}$ are the concentration of oxy-hemoglobin and deoxyhemoglobin, respectively:

$$SO_2 = \frac{C_{HbO_2}}{C_{HbO_2} + C_{Hb}} \quad (1)$$

In transmission mode pulse oximetry, light from LEDs is directed into the top of the finger and the transmitted light is sensed at the bottom of the finger by a photodetector. Beer-Lambert's law states that the intensity of light travelling through a medium decreases exponentially with distance. Transmission T is given by, $$T = I_0 \exp(-\varepsilon C d) \quad (2)$$

Here, $I_0$ is the incident light intensity, $\varepsilon$ is the molar absorptivity with units of L mM$^{-1}$cm$^{-1}$, C is the concentration of the absorbent medium, and d is the optical path length through the medium. The absorbance, A, is now defined as:

$$A = -\ln\frac{T}{I_0} = \varepsilon C d \quad (3)$$

Now considering attenuation in skin, tissue, and bones—represented with the subscript DC, and attenuation in oxy-hemoglobin and deoxyhemoglobin—represented with the subscripts $HbO_2$ and Hb, the following equations represent transmission at diastole and systole:

$$T_{high,dia} = I_0 \exp(-\varepsilon_{DC} C_{DC} d_{DC}) \exp(-\varepsilon_{HbO_2} C_{HbO_2} + \varepsilon_{Hb} C_{Hb}) d_{dia}) \quad (4)$$

$$T_{low,sys} = I_0 \exp(-\varepsilon_{DC} C_{DC} d_{DC}) \exp(-\varepsilon_{HbO_2} C_{HbO_2} + \varepsilon_{Hb} C_{Hb}) d_{sys}) \quad (5)$$

Light has to pass through the additional optical path $\Delta d$ at systole, therefore $d_{sys} = d_{dia} + \Delta d$. Additionally, a normalization step ($T_{normalized} = T/T_{high,dia}$) is required to determine the normalized systolic transmission. Now Eq. 3 can be rewritten by superpositioning absorbance of $HbO_2$ and HbO at a specific wavelength:

$$A = (\varepsilon_{HbO_2} S_a O_2 + \varepsilon_{Hb}(1 - S_a O_2))(C_{HbO_2} + C_{Hb}) \Delta d \quad (6)$$

$R_{os}$, the ratio of absorbed red ($A_{rd}$) and green ($A_{gr}$) light, depends on the normalized transmitted red ($T_{n,rd}$) and green ($T_{n,gr}$) light intensities. The ratio of the absorbance at red (rd) and green (gr) light can be found using the following equation:

$$R_{os} = \frac{A_{rd}}{A_{gr}} = \frac{(\varepsilon_{rd,HbO_2} S_a O_2 + \varepsilon_{rd,Hb}(1 - S_a O_2))(C_{HbO_2} + C_{Hb}) \Delta d}{(\varepsilon_{gr,HbO_2} S_a O_2 + \varepsilon_{gr,Hb}(1 - S_a O_2))(C_{HbO_2} + C_{Hb}) \Delta d} \quad (7)$$

Finally, arterial oxygen saturation ($S_a O_2$) can be calculated using Eq. 8. Here, $\varepsilon_{rd,Hb}$ and $\varepsilon_{gr,Hb}$ are the molar absorptivity of deoxyhemoglobin at red ($\lambda$=626 nm) and green ($\lambda$=532 nm) wavelengths. Similarly, $\varepsilon_{rd,HbO_2}$ and $\varepsilon_{gr,HbO_2}$ are the molar absorptivity of oxyhemoglobin at red ($\lambda$=626 nm) and green ($\lambda$=532 nm) wavelengths.

$$S_a O_2(R_{os}) = \frac{\varepsilon_{rd,Hb} - \varepsilon_{gr,Hb} R_{os}}{(\varepsilon_{rd,Hb} - \varepsilon_{rd,HbO_2}) + (\varepsilon_{gr,HbO_2} - \varepsilon_{gr,Hb}) R_{os}} \quad (8)$$

$S_a O_2$ vs $R_{os}$ for both red-infrared and red-green combinations are shown in FIG. 12A. However, empirical correction is required to overcome limitations of Beer-Lambert's Law in scattering tissue (versus a glass cuvette), which is given in FIG. 12B. The 11% offset in the calibration curves is experimentally obtained.

Organic Optoelectronic Oximeter Components:

OLED and OPD performance are both paramount to the oximeter measurement quality. The most important performance parameters are the spectral power of the OLEDs (FIG. 8B), and the EQE and short circuit current of the OPD (FIGS. 7D and 8B). As the OLEDs operating voltage increases, spectral power increases at the expense of efficiency, as shown by the increase of current with voltage at a higher rate than spectral power in FIG. 8B. For a pulse oximeter, this is an acceptable trade-off because higher spectral power from the OLEDs yields a better measurement signal.

Polyfluorene derivatives are selected in certain aspects as the emissive layer in the OLEDs due to their environmental stability, relatively high efficiencies, and self-assembling bulk-heterojunctions that can be tuned to emit at different wavelengths of the light spectrum. The green OLEDs were fabricated from a blend of poly(9,9-dioctylfluorene-co-n-(4-butylphenyl)-diphenylamine) (TFB) and poly((9,9-dioctyl-fluorene-2,7-diyl)-alt-(2,1,3-benzothiadiazole-4,8-diyl)) (F8BT). In these devices, electrons are injected into the F8BT phase of phase-separated bulk-heterojunction active layer while holes are injected into the TFB phase, forming excitons at the interfaces between the two phases and recombining in the lower energy F8BT phase for green emission. The emission spectrum of a representative device is shown in FIG. 7D. The red OLED was fabricated from a tri-blend blend of TFB, F8BT, and poly((9,9-dioctylfluo-rene-2,7-diyl)-alt-(4,7-bis(3-hexylthiophene-5-yl)-2,1,3-benzothiadiazole)-2,2-diyl) (TBT) with an emission peak of 626 nm as shown in FIG. 7D. The energy structure of the full stack used in the fabrication of OLEDs, where ITO/PEDOT:PSS is used as the anode, TFB as an electron blocking layer, and LiF/Al as the cathode, is shown in FIG. 8A. The OLED's physical structure is provided in FIG. 13. The red OLED operates similarly to the green, with the additional step of excitonic transfer via Förster energy transfer to the semiconductor with the lowest energy gap in the tri-blend, TBT, where radiative recombination occurs. The spectral power at 9 V for both types of OLEDs, green and red, was measured to be 20.1 mW/cm$^2$ and 5.83 mW/cm$^2$ respectively.

Figure 9A:
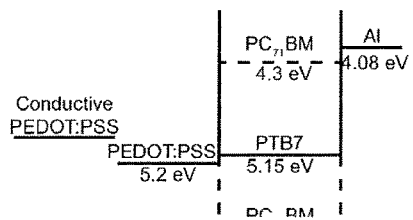
FIG. 9A shows and OPD energy structure.

An excellent OPD for oximetry should exhibit stable operation under ambient conditions with high external quantum efficiencies (EQEs) at the peak OLED emission wavelengths (e.g., 532 nm and 626 nm). Additionally, a high short circuit current is desirable, from which the pulse and oxygenation values are derived. Thieno[3,4-b]thiophene/benzo-dithiophene (PTB7) mixed with [6,6]-phenyl C71-butyric acid methyl ester (PC$_{71}$BM) is a stable donor:acceptor bulk heterojunction OPD system which yields EQE as high as 50%. The transparent electrode and active layer of the OPD are printed on a plastic substrate using a surface tension assisted blade coating technique. FIG. 9A shows the energy band structure of the device including the transparent electrode (a high conductivity/high work function PEDOT:PSS bilayer) and an Al cathode. The physical device structure of the OPD is shown in FIG. 13. The EQE at 532 nm and 626 nm is 38% and 47% respectively at short circuit, as shown in FIG. 7D, and the leakage current of 1 nA/cm$^2$ at 2 V applied reverse bias is shown in FIG. 9B together with the photocurrent when the device is illuminated with a 355 uW/cm$^2$ light source at 640 nm.

Figure 9B:
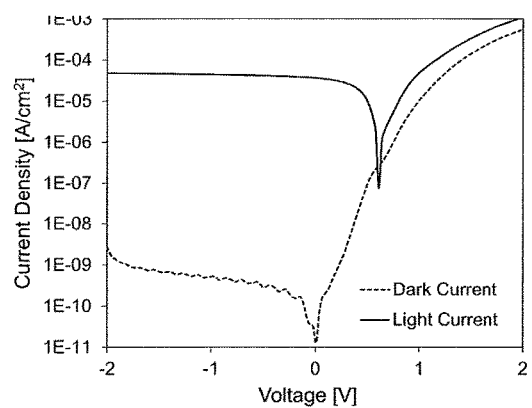
FIG. 9B shows light current (red solid line) with excitation from a 640 nm, 355 μW/cm$^2$ light source and dark current (black dashed line) as a function of applied voltage.

Despite the low reverse bias leakage current shown in FIG. 9B, the OPD was biased at 0V, the short-circuit condition, in order to sense low photocurrent levels. The frequency response of both the OPD and OLEDs was also characterized, since oximetry is usually performed at 1 KHz. The 3 dB cut-off was found to be at frequencies higher than 10 KHz for the all-organic optoelectronic sensor, which is significantly higher than oximetry's operational frequency (FIG. 15). Notably, the frequency performance of the OPD is not hampered at short-circuit because the shunt capacitance of organic photodiodes decreases negligibly with reverse bias, unlike inorganic photodiodes.

Figure 10A:
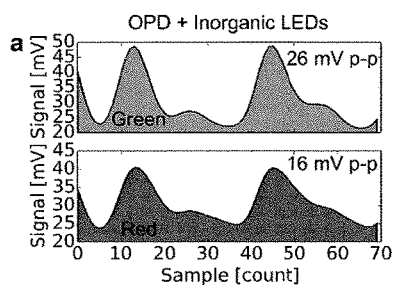
FIG. 10A shows Photoplethysmogram (PPG) acquisition using combinations of inorganic and organic LEDs and photodiodes (PDs); a PPG signal acquired using inorganic red and green LEDs and an OPD. Green and red PPG signal amplitudes of 26 mVp-p and 16 mVp-p were obtained, respectively.
Figure 10B:
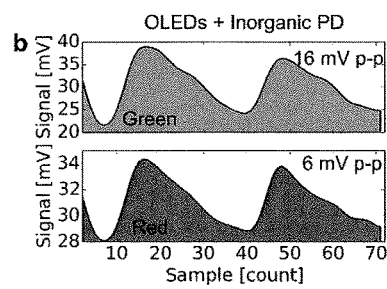
FIG. 10B shows a PPG Signal acquired using OLEDs and silicon PD—absence of lensing epoxy and reduced optical power of the OLEDs bring down signal magnitude to 16 mVp-p and 6 mVp-p for green and red excitation.
Figure 10C:
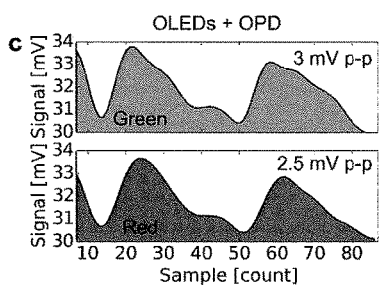
FIG. 10C shows a PPG signal acquired using OLEDs and OPD; although signal magnitudes are reduced to 3 mVp-p and 2.5 mVp-p, the signal is sufficient for resolving the PPG waveform and provide light absorbance ratio information for arterial blood oxygenation calculation.

The observed OLED spectral power for both red and green wavelengths is sufficient for the transmission of light through the finger and the signal acquired by the organic photodetector is sufficiently high for resolving the pulsating photoplethysmogram (PPG) signal shown in FIG. 7B. The pulse waveforms (two cardiac cycles) generated with a combination of organic and inorganic devices are shown in FIG. 10. The PPG obtained when a human finger is illuminated by inorganic LEDs and the transmitted light is measured with an OPD is shown in FIG. 10A. When the same measurement is performed using OLEDs and a conventional Si photodiode (FIG. 10B) the magnitude of the PPG signal is reduced from 26 mVp-p to 16 mVp-p for the green and 16 mVp-p to 6 mVp-p for the red due to the lower optical power of the organic LEDs compared to their inorganic equivalent device. Finally both OLEDs and an OPD are used to obtain a PPG under the same experimental conditions (FIG. 10C), yielding signal magnitudes of 3 mVp-p for the green and 2.5 mVp-p for the red. It is clear that the magnitude of the signal is substantially reduced with the introduction of organic-based devices, but the PPG obtained at red and green wavelengths yield similar shapes for all device combinations shown in FIG. 10, which will result in similar pulse and arterial oxygenation values. The lower signal magnitude shown by the organic probe is compensated for by increasing the area of devices, resulting in higher photocurrents which directly translate into higher PPG signals, as shown in FIG. 14A.

System Design for an Organic Optoelectronic Pulse Oximeter

The organic pulse oximetry sensor composed of two red and green OLED arrays and an OPD (FIG. 11A) is interfaced with a microcontroller which drives the OLEDs, measures the OPD signal, and transfers the data to a computer for analysis (FIG. 11B). The obtained signal from the OPD passes through an analog front-end where the PPG signal is filtered and amplified. The pulsating part of the signal yields heart rate and oxygenation according to empirical correction to Eq. 8. The accuracy of the organic optoelectronic sensor is characterized and calibrated by comparing pulse and oxygenation measurements taken simultaneously by the organic optoelectronic sensor and a commercially available pulse oximeter. The resultant pulse waveforms, pulse value, ratio of absorbed light, and arterial blood oxygen saturation from the red and near-infrared LEDs in the inorganic oximeter and the red and green OLEDs in the organic oximeter are shown in FIGS. 11C and 11D, respectively. The OLEDs are powered by a 9 V battery and the OPD is biased at 0 V. The AC component of the signal (FIG. 7B) is essential for visualizing cardiac rhythm and computing arterial blood oxygen saturation. The OPD read-out circuit includes two internal operational amplifiers (op-amps) (FIG. 11B) in which the first stage amplifies the whole PPG signal from the photodiode. The second stage only amplifies the pulsating part of the signal and is read by an analog-to-digital converter (ADC). With two-stage amplification, a 50-60 mVp-p PPG signal was obtained for the inorganic probe (FIG. 11C) and a 3-4 mVp-p PPG signal for the organic probe (FIG. 11D). The heart rate and ratio of transmitted light at two wavelengths (FIGS. 11C and 11D) was calculated directly from the PPG signals and the arterial blood oxygen saturation was derived from the ratio of transmitted light, as discussed herein. The calculated heart rate and oxygenation derived from the PPG signals from the inorganic and organic probes are both 65-70 bpm and 94-96%, respectively (FIGS. 11C and 11D). A 1% error for pulse rate and 2% error for oxygenation were observed when comparing the organic optoelectronic sensor to the inorganic sensor.

The novel combination of red and green OLEDs, as opposed to a red and near-infrared LED pair, is successfully implemented in pulse oximetry because the difference in the absorptivity of oxygenated and deoxygenated hemoglobin at the green wavelength is comparable to the difference at near-infrared wavelengths as seen in FIG. 7C. Green LEDs have not been used conventionally because shorter wavelengths are more efficiently absorbed by the body. However, the higher spectral power output of the green OLEDs (FIG. 8B) compensates for any absorption losses in non-pulsating blood and tissue, as can be inferred from the higher green signal amplitudes in FIG. 10 compared to the red signal amplitudes. An empirical correction was employed to calculate arterial blood oxygenation from the ratio of transmitted green and red light, a scheme widely used for correcting for the deviation from Beer-Lambert's Law (which doesn't account for the scattering that occurs in human tissue) in red and near-infrared pulse oximetry measurements.

Aside from maximizing OPD EQE and short circuit photocurrent and OLED spectral power, the OPD's short circuit current resulting from excitation by ambient light should be minimized in order to achieve the best pulse oximetry signal, as parasitic photodetector current from ambient light is a contributor to conventional pulse oximetry failure. The effects of ambient light on the OPD's short circuit current were measured using two finger phantoms with radii of 9 mm and 5 mm, representative of the wide range of human finger sizes. Flexing the photodiode around the finger phantom, as opposed to taking the measurement with the photodiode placed flat, non-flexed, against the phantom, significantly reduces the parasitic short circuit current produced by ambient light. Under typical ambient room light conditions of 72-76 1¼ W/cm$^2$, flexing the OPD around the 9 mm and 5 mm radii phantoms reduced the parasitic current from 270 nA to 20 nA and 280 nA to 60 nA, respectively (FIG. 14). The ability of the flexible OPD to conform around the human body therefore improves the pulse oximeter's reliability.

The organic optoelectronic pulse oximetry sensor described here demonstrates the potential for the application of organic electronics to thrive in the medical device field. If implemented in a disposable bandage form factor, an organic optoelectronic medical sensor does not face the stability issues that have hindered organic electronics in long-term applications such as displays and energy harvesting due to the substantially shorter device lifetime required.

Rather, the large-area scalability, inexpensive processing and flexibility of organic optoelectronics will allow medical sensors to be made in new shapes and sizes, diversifying possible sensing locations on the human body, enabling medical professionals to better monitor their patients care.

OLED Fabrication and Characterization

The semiconducting polymers used in the emissive layer of the OLEDs were supplied by Cambridge Display Technologies Ltd. The red OLED active layer was made from a 25:70:5 blend of TFB:F8BT:TBT in a 10 mg/mL o-xylene solution. The green OLED active layer was made from a 1:9 blend of TFB:F8BT in a 10 mg/mL o-xylene solution. Patterned ITO-substrates were cleaned via sonication in acetone and then isopropyl alcohol. The substrate surfaces were made hydrophilic with a 2 minute plasma treatment prior to spincoating a 40 nm layer of Clevios PEDOT:PSS AI4083. Any remaining moisture was evaporated in a 10 minute annealing step at 120° C. before moving the samples into a nitrogen glovebox for the remainder of the fabrication procedure. TFB was spin-coated from a 10 mg/mL o-xylene solution and then annealed at 180° C. for 45 minutes before cooling and spin-rinsing with o-xylene, producing a 10-20 nm thick electron blocking layer. The active layer was then spun at 4500 rpm for a 100 nm film thickness. The LiF (1 nm)/Al (100 nm) cathode was thermally evaporated under vacuum at $4*10^{-6}$ Torr. Finished devices were encapsulated with UV-curable Delo Katiobond LP612 epoxy and clean quartz glass. OLED current/voltage characteristics and spectral power measurements were taken with an Orb Optronix light measurement system complete with an Orb Optronix SP-50 spectrometer, integrating sphere, Keithley 2400 SourceMeter, and Spectral Suite 3.0 software.

OPD Fabrication and Characterization

OPDs were printed on top of planarized PEN substrates (DuPont) using a blade coating technique. A layer of high conductivity PEDOT:PSS (Sigma Aldrich 739316-25G) was printed by blade coating (200 μm blade height at 1.6 cm/s) the solution over a large hydrophilic strip in the substrate defined by a 10 second plasma treatment through a stencil. Following a 10 minute anneal at 120° C. a layer of high work function PEDOT:PSS (Clevios Al4083) was coated and annealed over the previous print using the same process. The active layer ink comprised of a 1:1 weight ratio of PTB7:$PC_{71}BM$ (Solaris Chem) dissolved to 35 mg/mL in chlorobenzene with a 3 vol. % concentration of 1,8-diiodooctane and was blade coated (350 μm blade height at 1.6 cm/s) in a glove box with the substrate heated to 40° C. The aluminum cathode (100 nm) was thermally evaporated under vacuum at $4*10^{-6}$ Torr. Finished devices were encapsulated with UV-curable Delo Katiobond LP612 epoxy and Saran wrap after being post-annealed at 120° C. for 10 minutes. All OLED and organic photodiode layer thicknesses were measured with a Dektak Profilometer.

Electronic Hardware and Software for Data Acquisition and Processing

The Texas Instruments MSP430 microcontroller was chosen for data acquisition and processing because of its built-in analog to digital converters (ADCs) and digital to analog converters (DACs), which are required for the pulse oximeter. General purpose input output (GPIO) pins from the microcontroller control LED switching, ADCs are utilized to read the amplified OPD signal from the multiplexer, and DACs are used to control LED intensity and in the DC signal amplification stage. The LEDs are operated in a sequential approach, so that only one of the LEDs is on at a particular moment. 512 samples are taken from each of the LEDs in a second. A software trigger from the microcontroller controls a PNP BJT switch that triggers the LED on/off. Additionally, DACs are used to control the drive current for the LEDs using a NPN transistor. For ensuring compatibility with the organic LEDs, signals from the microcontroller are shifted to 9 V using general purpose operational amplifiers (op-amps). Finally, universal asynchronous receiver/transmitter (UART) protocol is used to send processed data to a computer for visualization. A modular approach was used by separating the LED driver circuit and OPD read circuit, simplifying circuit design and debugging.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the embodiments (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the embodiments of the disclosure unless otherwise claimed. No language in the specification should be construed as indicating any non-claimed element as essential to the practice the embodiments of the disclosure.

Various embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this specification includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A pulse oximeter device, comprising:
    an array of first light emitting elements configured to emit red light, wherein each first light emitting element in the array of first light emitting elements comprises a first printed organic light emitting diode (OLED);
    an array of second light emitting elements configured to emit green light or infrared light, wherein each second light emitting element in the array of second light emitting elements comprises a second printed OLED;

an array of sensor elements configured to detect red and green light or red and infrared light and output signals representing detected red and green light or detected red and infrared light, wherein each sensor element in the array of sensor elements comprises a printed organic photodiode; and a flexible substrate, wherein the array of first light emitting elements, the array of second light emitting elements and the array of sensor elements are printed on the flexible substrate.

2. The pulse oximeter device of claim 1, wherein the flexible substrate comprises polyethylene napthalate (PEN).

3. The pulse oximeter device of claim 1, wherein each sensor element is configured to detect the emitted red and green light or the emitted red and infrared light transmitted through tissue containing blood.

4. The pulse oximeter device of claim 1, wherein each sensor element is configured to detect the emitted red and green light or the emitted red and infrared light reflected by tissue containing blood.

5. The pulse oximeter device of claim 1, further comprising a signal processing element configured to receive and process the signals representing detected red and green light or detected red and infrared light output by the array of sensor elements to produce signals that represent blood oxygenation content.

6. A pulse oximeter device, comprising:
a plurality of first light emitting elements configured to emit red light, wherein each first light emitting element of the plurality of first light emitting elements comprises a first printed organic light emitting diode (OLED);
a plurality of second light emitting elements configured to emit green light or infrared light, wherein each second light emitting element of the plurality of second light emitting elements comprises a second printed OLED;
a plurality of sensor elements configured to detect red and green light or red and infrared light and output signals representing detected red and green light or detected red and infrared light, wherein each sensor element in the plurality of sensor elements comprises a printed organic photodiode; and
a flexible substrate, wherein the first light emitting elements, the second light emitting elements and the sensor elements are printed on the flexible substrate.

7. The pulse oximeter device of claim 6, wherein the flexible substrate comprises polyethylene napthalate (PEN).

8. The pulse oximeter device of claim 6, wherein the sensor elements are configured to detect the emitted red and green light or the emitted red and infrared light transmitted through tissue containing blood.

9. The pulse oximeter device of claim 6, wherein the sensor elements are configured to detect the emitted red and green light or the emitted red and infrared light reflected by tissue containing blood.

10. The pulse oximeter device of claim 6, further comprising a signal processing element configured to receive and process the signals representing detected red and green light or detected red and infrared light output by the sensor elements to produce signals representing blood oxygenation content.

11. A method of measuring blood oxygenation content of a tissue sample, the method comprising:
applying a flexible pulse oximeter device proximal the tissue sample, the flexible pulse oximeter device including:
a flexible substrate;
at least one first printed light emitting element formed on the flexible substrate and configured to emit red light;
at least one second printed light emitting element formed on the flexible substrate and configured to emit green light or infrared light; and
at least one printed sensor element formed on the flexible substrate and configured to detect red and green light or red and infrared light and output signals representing detected red and green light or detected red and infrared light;
activating the at least one first printed light emitting element and the at least one second printed light emitting element;
detecting red and green light or red and infrared light reflected by the tissue sample by the at least one printed sensor element; and
outputting signals representing the detected reflected red and green light or the detected red and infrared light to a signal processing device.

12. The method of claim 11, wherein each of the at least one first printed light emitting element and the at least one second printed light emitting element comprises an organic LED, and wherein the at least one printed sensor element comprises an organic photodiode.

13. A method of mapping blood oxygenation content of a region of a tissue sample, the method comprising:
a) applying a flexible pulse oximeter device proximal the tissue sample, the flexible pulse oximeter device including:
a flexible substrate;
an array of first light emitting elements formed on the flexible substrate configured to emit red light;
an array of second light emitting elements formed on the flexible substrate configured to emit green light or infrared light; and
an array of sensor elements formed on the flexible substrate that detects red and green light or that detects red and infrared light and that outputs signals representing detected red and green light or detected red and infrared light;
b) activating a first portion of the array of first light emitting elements and a first portion of the array of second light emitting elements;
c) detecting red and green light or red and infrared light reflected by the tissue sample by a first sensor element; and
d) outputting, by the first sensor element, signals representing the detected reflected red and green light or the detected reflected red and infrared light to a signal processing device;
e) activating a second portion of the array of first light emitting elements, and a second portion of the array of second light emitting elements;
f) detecting red and green light or red and infrared light reflected by the tissue sample by a second sensor element; and
g) outputting, by the second sensor element, signals representing the detected reflected red and green light or the detected reflected red and infrared light to a signal processing device; and
h) processing the signals output by the first sensor element and the second sensor element to determine blood circulation and oxygenation content for different areas of the region of the tissue sample.

14. The method of claim 13, wherein the steps e)-g) are performed after steps b)-d).

15. The method of claim 13, wherein the steps e)-g) are performed simultaneously with steps b)-d).

16. The method of claim 13, wherein each first light emitting element of the array of the first light emitting elements and each second light emitting the array of second light emitting elements comprises an organic LED, and wherein each sensor element of the array of sensor elements comprises an organic photodiode.

17. The method of claim 13, wherein each first light emitting element of the array of the first light emitting elements and each second light emitting element of the array of second light emitting elements comprises a printed organic LED, and wherein each sensor element of the array of sensor elements comprises a printed organic photodiode.

* * * * *